(12) United States Patent
Dreyfuss et al.

(10) Patent No.: US 12,064,104 B2
(45) Date of Patent: *Aug. 20, 2024

(54) FULLY-THREADED BIOABSORBABLE SUTURE ANCHOR

(71) Applicant: Arthrex, Inc., Naples, FL (US)

(72) Inventors: Peter J. Dreyfuss, Naples, FL (US); Stephen S. Burkhart, Boerne, TX (US)

(73) Assignee: Arthrex, Inc., Naples, FL (US)

( * ) Notice: Subject to any disclaimer, the term of this patent is extended or adjusted under 35 U.S.C. 154(b) by 106 days.

This patent is subject to a terminal disclaimer.

(21) Appl. No.: 17/739,806

(22) Filed: May 9, 2022

(65) Prior Publication Data
US 2022/0401096 A1 Dec. 22, 2022

Related U.S. Application Data

(63) Continuation of application No. 16/784,612, filed on Feb. 7, 2020, now Pat. No. 11,324,493, which is a
(Continued)

(51) Int. Cl.
*A61B 17/04* (2006.01)
*A61L 17/10* (2006.01)
(Continued)

(52) U.S. Cl.
CPC .......... *A61B 17/0401* (2013.01); *A61L 17/10* (2013.01); *A61L 17/145* (2013.01);
(Continued)

(58) Field of Classification Search
CPC ................. A61B 2017/044; A61B 2017/0458
See application file for complete search history.

(56) References Cited

U.S. PATENT DOCUMENTS

| 74,489 A | 2/1868 | Bidwell |
| 85,794 A | 1/1869 | Crosby |
(Continued)

FOREIGN PATENT DOCUMENTS

| CA | 2045903 | 6/1991 |
| EP | 0465910 A1 | 1/1992 |
(Continued)

OTHER PUBLICATIONS

Hand-drawn Diagram Showing Cortical Layer. Slocum, Apr. 27, 2017. Slocum Exhibit 7 from *Smith & Nephew v. Arthrex*, Case IPR 2016-00918.
(Continued)

*Primary Examiner* — Alexander J Orkin
(74) *Attorney, Agent, or Firm* — Carlson, Gaskey & Olds, P.C.

(57) ABSTRACT

A suture anchor includes an anchor body having a longitudinal axis, a proximal end, and a distal end. The anchor body includes a central bore located at the proximal end and a passage extending between the central bore and the distal end. The central bore has a first dimension substantially perpendicular to the longitudinal axis, and the passage has a second dimension substantially perpendicular to the longitudinal axis less than the first dimension. The suture anchor includes a flexible strand extending through the passage, and a first knot formed in the flexible strand at the distal end has a third dimension greater than the second dimension to prevent the first knot from passing through the passage. A closed loop is positionable at least partially within the central bore and formed entirely by the flexible strand without forming any additional knots on the flexible strand extending proximally from the first knot.

20 Claims, 14 Drawing Sheets

Related U.S. Application Data continuation of application No. 15/382,855, filed on Dec. 19, 2016, now Pat. No. 10,595,847, which is a continuation of application No. 11/224,060, filed on Sep. 13, 2005, now Pat. No. 9,521,999.

(51) Int. Cl.
*A61L 17/14* (2006.01)
*A61B 17/00* (2006.01)

(52) U.S. Cl.
CPC .............. *A61B 2017/00004* (2013.01); *A61B 2017/0409* (2013.01); *A61B 2017/0414* (2013.01); *A61B 2017/044* (2013.01); *A61B 2017/0445* (2013.01); *A61B 2017/0458* (2013.01)

(56) References Cited

U.S. PATENT DOCUMENTS

| | | |
|---|---|---|
| 176,335 A | 4/1876 | Morton |
| 463,650 A | 11/1891 | Stevens |
| 1,379,606 A | 5/1921 | Ashley |
| 1,574,578 A | 2/1926 | Holmes |
| 1,610,309 A | 12/1926 | Niederer |
| 1,925,174 A | 9/1933 | Creamean |
| 2,045,903 A | 6/1936 | Fortin |
| 2,121,193 A | 6/1938 | Hanicke |
| 2,243,717 A | 5/1941 | Moreira |
| 2,329,398 A | 9/1943 | Duffy |
| 2,381,050 A | 8/1945 | Hardinge |
| 2,397,216 A | 3/1946 | Stellin |
| 2,490,364 A | 2/1948 | Livingston |
| 2,472,103 A | 6/1949 | Giesen |
| 2,489,870 A | 11/1949 | Dzus |
| 2,562,419 A | 7/1951 | Ferris |
| 2,570,465 A | 10/1951 | Lundholm |
| 2,699,774 A | 1/1955 | Livingston |
| 2,787,186 A | 4/1957 | Brogiotti |
| 2,817,339 A | 12/1957 | Sullivan |
| 2,890,734 A | 6/1959 | Mullin |
| 3,143,916 A | 8/1964 | Rice |
| 3,420,929 A | 1/1969 | Morin |
| 3,575,080 A | 4/1971 | Hannay |
| 3,579,831 A | 5/1971 | Stevens |
| 3,584,667 A | 6/1971 | Reiland |
| 3,664,400 A | 5/1972 | Moore |
| 3,716,058 A | 2/1973 | Tanner, Jr. |
| 3,768,635 A | 10/1973 | Eggert |
| 3,842,825 A | 10/1974 | Wagner |
| 3,861,269 A | 1/1975 | Laverty |
| 3,910,281 A | 10/1975 | Kletschka et al. |
| 3,910,282 A | 10/1975 | Messer et al. |
| 3,951,261 A | 4/1976 | Mandel et al. |
| 3,990,438 A | 11/1976 | Pritchard |
| 4,006,657 A | 2/1977 | Dunnette |
| 4,006,747 A | 2/1977 | Kronenthal et al. |
| 4,013,071 A | 3/1977 | Rosenberg |
| 4,041,939 A | 8/1977 | Hall |
| 4,114,508 A | 9/1978 | Jeal |
| 4,135,623 A | 1/1979 | Thyen |
| 4,175,555 A | 11/1979 | Herbert |
| 4,222,689 A | 9/1980 | Fujiwara |
| 4,241,638 A | 12/1980 | Shimizu et al. |
| 4,244,370 A | 1/1981 | Furlow et al. |
| 4,250,674 A | 2/1981 | Feist |
| 4,275,717 A | 6/1981 | Bolesky |
| 4,289,124 A | 9/1981 | Zickel |
| 4,301,551 A | 11/1981 | Dore et al. |
| 4,329,099 A | 5/1982 | Shimizu et al. |
| 4,351,069 A | 9/1982 | Ballintyn et al. |
| 4,406,623 A | 9/1983 | Grafelmann et al. |
| 4,419,029 A | 12/1983 | Wenzel |
| 4,424,898 A | 1/1984 | Thyen et al. |
| 4,454,875 A | 6/1984 | Pratt et al. |
| 4,467,478 A | 8/1984 | Jurgutis |
| 4,468,200 A | 8/1984 | Munch |
| 4,483,023 A | 11/1984 | Hoffman, Jr. et al. |
| 4,507,817 A | 4/1985 | Staffeld |
| 4,519,100 A | 5/1985 | Wills et al. |
| 4,520,511 A | 6/1985 | Gianezio et al. |
| 4,537,185 A | 8/1985 | Stednitz |
| 4,539,981 A | 9/1985 | Tunc |
| 4,569,338 A | 2/1986 | Edwards |
| 4,590,928 A | 5/1986 | Hunt et al. |
| 4,597,776 A | 7/1986 | Ullman et al. |
| 4,601,625 A | 7/1986 | Ernst et al. |
| 4,605,414 A | 8/1986 | Czajka |
| 4,611,580 A | 9/1986 | Wu |
| 4,632,100 A | 12/1986 | Somers et al. |
| 4,633,869 A | 1/1987 | Schmieding |
| 4,640,271 A | 2/1987 | Lower |
| 4,672,957 A | 6/1987 | Hourahane |
| 4,693,654 A | 9/1987 | Bettini |
| 4,712,542 A | 12/1987 | Daniel et al. |
| 4,723,541 A | 2/1988 | Reese |
| 4,738,255 A | 4/1988 | Goble et al. |
| 4,741,330 A | 5/1988 | Hayhurst |
| 4,750,492 A | 6/1988 | Jacobs |
| 4,756,653 A | 7/1988 | Berger |
| 4,784,126 A | 11/1988 | Hourahane |
| 4,815,467 A | 3/1989 | Chestnut |
| 4,870,957 A | 10/1989 | Goble et al. |
| 4,892,429 A | 1/1990 | Giannuzzi |
| 4,898,156 A | 2/1990 | Gatturna et al. |
| 4,946,467 A | 8/1990 | Ohi et al. |
| 4,946,468 A | 8/1990 | Li |
| 4,963,144 A | 10/1990 | Huene |
| 4,976,715 A | 12/1990 | Bays et al. |
| 4,978,350 A | 12/1990 | Wagenknecht |
| 4,988,351 A | 1/1991 | Paulos et al. |
| 5,002,550 A | 3/1991 | Li |
| 5,002,563 A | 3/1991 | Pyka et al. |
| 5,019,079 A | 5/1991 | Ross |
| 5,037,422 A | 8/1991 | Hayhurst et al. |
| 5,041,129 A | 8/1991 | Hayhurst et al. |
| 5,047,030 A | 9/1991 | Draenert |
| 5,059,077 A | 10/1991 | Schmid |
| 5,059,201 A | 10/1991 | Asnis |
| 5,061,181 A | 10/1991 | Niznick |
| 5,067,956 A | 11/1991 | Buford, III et al. |
| 5,074,790 A | 12/1991 | Bauer |
| 5,084,050 A | 1/1992 | Draenert |
| 5,087,201 A | 2/1992 | Mondani et al. |
| 5,100,417 A | 3/1992 | Cerier et al. |
| 5,100,471 A | 3/1992 | Winnik et al. |
| 5,102,414 A | 4/1992 | Kirsch |
| 5,102,421 A | 4/1992 | Anspach, Jr. |
| 5,108,397 A | 4/1992 | White |
| 5,116,178 A | 5/1992 | Lerman et al. |
| 5,120,171 A | 6/1992 | Lasner |
| 5,120,172 A | 6/1992 | Wakai |
| 5,129,901 A | 7/1992 | Decoste |
| 5,139,499 A | 8/1992 | Small et al. |
| 5,139,520 A | 8/1992 | Rosenberg |
| 5,141,520 A | 8/1992 | Goble et al. |
| D330,591 S | 10/1992 | Rosenberg et al. |
| 5,152,790 A | 10/1992 | Rosenberg et al. |
| 5,156,616 A | 10/1992 | Meadows et al. |
| 5,163,960 A | 11/1992 | Bonutti |
| D331,463 S | 12/1992 | Rosenberg et al. |
| 5,176,682 A | 1/1993 | Chow |
| 5,180,382 A | 1/1993 | Frigg et al. |
| 5,205,746 A | 4/1993 | Chanavaz |
| 5,207,679 A | 5/1993 | Li |
| 5,211,647 A | 5/1993 | Schmieding |
| 5,217,486 A | 6/1993 | Rice et al. |
| 5,224,946 A | 7/1993 | Hayhurst et al. |
| 5,236,445 A | 8/1993 | Hayhurst et al. |
| 5,242,447 A | 9/1993 | Borzone |
| 5,246,369 A | 9/1993 | Poulmaire |
| 5,246,441 A | 9/1993 | Ross et al. |
| 5,250,055 A | 10/1993 | Moore et al. |
| 5,258,016 A | 11/1993 | DiPoto et al. |

(56) References Cited

U.S. PATENT DOCUMENTS

| | | |
|---|---|---|
| 5,261,914 A | 11/1993 | Warren |
| 5,268,001 A | 12/1993 | Nicholson et al. |
| 5,275,176 A | 1/1994 | Chandler |
| 5,285,016 A | 2/1994 | Narizuka et al. |
| 5,306,290 A | 4/1994 | Martins et al. |
| 5,312,412 A | 5/1994 | Whipple |
| 5,312,438 A | 5/1994 | Johnson |
| 5,320,626 A | 6/1994 | Schmieding |
| 5,324,308 A | 6/1994 | Pierce |
| 5,326,205 A | 7/1994 | Anspach, Jr. et al. |
| 5,327,896 A | 7/1994 | Schmieding |
| 5,330,468 A | 7/1994 | Burkhart |
| 5,334,204 A | 8/1994 | Clewett et al. |
| 5,336,240 A | 8/1994 | Metzler et al. |
| 5,350,383 A | 9/1994 | Schmieding et al. |
| 5,354,298 A | 10/1994 | Lee et al. |
| 5,356,413 A | 10/1994 | Martins et al. |
| 5,356,435 A | 10/1994 | Thein |
| 5,360,448 A | 11/1994 | Thramann |
| 5,364,400 A | 11/1994 | Rego, Jr. et al. |
| 5,370,661 A | 12/1994 | Branch |
| 5,370,662 A | 12/1994 | Stone et al. |
| 5,375,956 A | 12/1994 | Pennig |
| 5,376,119 A | 12/1994 | Zimmermann et al. |
| 5,380,334 A | 1/1995 | Torrie et al. |
| 5,383,905 A | 1/1995 | Golds et al. |
| D357,534 S | 4/1995 | Hayes |
| 5,403,136 A | 4/1995 | Mathys |
| 5,411,506 A | 5/1995 | Goble et al. |
| 5,411,523 A | 5/1995 | Goble |
| 5,414,966 A | 5/1995 | Montoya |
| 5,417,533 A | 5/1995 | Lasner |
| 5,417,691 A | 5/1995 | Hayhurst |
| 5,417,712 A | 5/1995 | Whittaker et al. |
| D359,557 S | 6/1995 | Hayes |
| 5,423,860 A | 6/1995 | Lizardi et al. |
| 5,441,502 A | 8/1995 | Bartlett |
| 5,441,508 A | 8/1995 | Gazielly et al. |
| 5,443,482 A | 8/1995 | Stone et al. |
| 5,447,401 A | 9/1995 | Jones et al. |
| 5,451,225 A | 9/1995 | Ross, Jr. et al. |
| 5,456,267 A | 10/1995 | Stark |
| 5,456,685 A | 10/1995 | Huebner |
| 5,458,602 A | 10/1995 | Goble et al. |
| 5,458,608 A | 10/1995 | Wortich |
| 5,462,644 A | 10/1995 | Woodson |
| 5,464,425 A | 11/1995 | Skiba |
| 5,464,427 A | 11/1995 | Curtis et al. |
| 5,466,243 A | 11/1995 | Schmieding et al. |
| 5,470,334 A | 11/1995 | Ross et al. |
| 5,480,403 A | 1/1996 | Lee et al. |
| 5,486,197 A | 1/1996 | Le et al. |
| 5,489,210 A | 2/1996 | Hanosh |
| 5,492,442 A | 2/1996 | Lasner |
| 5,496,326 A | 3/1996 | Johnson |
| 5,501,695 A | 3/1996 | Anspach, Jr. et al. |
| 5,501,696 A | 3/1996 | Trott |
| 5,505,735 A | 4/1996 | Li |
| 5,505,736 A | 4/1996 | Reimels et al. |
| 5,520,692 A | 5/1996 | Ferrante |
| 5,522,843 A | 6/1996 | Zang |
| 5,522,844 A | 6/1996 | Johnson |
| 5,522,845 A | 6/1996 | Wenstrom, Jr. |
| 5,527,342 A | 6/1996 | Pietrzak et al. |
| 5,531,748 A | 7/1996 | de la Caffiniere |
| 5,534,001 A | 7/1996 | Schlapfer et al. |
| 5,534,011 A | 7/1996 | Greene, Jr. et al. |
| 5,534,031 A | 7/1996 | Matsuzaki et al. |
| 5,540,718 A | 7/1996 | Bartlett |
| 5,545,180 A | 8/1996 | Le et al. |
| 5,549,617 A | 8/1996 | Green et al. |
| 5,549,677 A | 8/1996 | Durr et al. |
| 5,556,428 A | 9/1996 | Shah |
| 5,562,664 A | 10/1996 | Durlacher et al. |
| 5,562,672 A | 10/1996 | Huebner et al. |
| 5,562,689 A | 10/1996 | Green et al. |
| 5,569,305 A | 10/1996 | Bonutti |
| 5,569,306 A | 10/1996 | Thal |
| 5,571,139 A | 11/1996 | Jenkins, Jr. |
| 5,573,547 A | 11/1996 | LeVeen et al. |
| 5,573,548 A | 11/1996 | Nazre et al. |
| 5,575,801 A | 11/1996 | Habermeyer et al. |
| 5,575,819 A | 11/1996 | Amis |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,839 A | 12/1996 | Gieringer |
| 5,584,860 A | 12/1996 | Goble et al. |
| 5,591,207 A | 1/1997 | Coleman |
| 5,593,410 A | 1/1997 | Vrespa |
| 5,593,425 A | 1/1997 | Bonutti et al. |
| 5,601,557 A | 2/1997 | Hayhurst |
| 5,601,558 A | 2/1997 | Torrie et al. |
| 5,607,432 A | 3/1997 | Fucci |
| 5,618,314 A | 4/1997 | Harwin et al. |
| 5,624,446 A | 4/1997 | Harryman, II |
| 5,626,612 A | 5/1997 | Bartlett |
| 5,626,613 A | 5/1997 | Schmieding |
| 5,628,766 A | 5/1997 | Johnson |
| 5,630,814 A | 5/1997 | Ross, Jr. et al. |
| 5,630,815 A | 5/1997 | Pohl et al. |
| 5,634,926 A | 6/1997 | Jobe |
| 5,637,112 A | 6/1997 | Moore et al. |
| 5,642,996 A | 7/1997 | Mochida et al. |
| 5,643,269 A | 7/1997 | Harle |
| 5,643,273 A | 7/1997 | Clark |
| 5,643,320 A | 7/1997 | Lower et al. |
| 5,643,321 A | 7/1997 | McDevitt |
| 5,645,545 A | 7/1997 | Bryant |
| 5,645,547 A | 7/1997 | Coleman |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,112 A | 9/1997 | Thal |
| 5,667,509 A | 9/1997 | Westin |
| D385,352 S | 10/1997 | Bales et al. |
| 5,676,665 A | 10/1997 | Bryan |
| 5,681,318 A | 10/1997 | Pennig et al. |
| 5,681,333 A | 10/1997 | Burkhart et al. |
| 5,683,401 A | 11/1997 | Schmieding et al. |
| 5,683,418 A | 11/1997 | Luscombe et al. |
| 5,683,419 A | 11/1997 | Thal |
| 5,685,313 A | 11/1997 | Mayevsky |
| 5,690,649 A | 11/1997 | Li |
| 5,690,676 A | 11/1997 | DiPoto et al. |
| 5,690,677 A | 11/1997 | Schmieding et al. |
| 5,693,060 A | 12/1997 | Martin |
| 5,694,783 A | 12/1997 | Bartlett |
| 5,697,950 A | 12/1997 | Fucci et al. |
| 5,702,397 A | 12/1997 | Goble et al. |
| 5,702,398 A | 12/1997 | Tarabishy |
| 5,702,422 A | 12/1997 | Stone |
| 5,703,687 A | 12/1997 | Kumagai et al. |
| 5,707,373 A | 1/1998 | Sevrain et al. |
| 5,707,394 A | 1/1998 | Miller et al. |
| 5,709,708 A | 1/1998 | Thal |
| 5,713,900 A | 2/1998 | Benzel et al. |
| 5,720,765 A | 2/1998 | Thal |
| 5,720,766 A | 2/1998 | Zang et al. |
| 5,725,529 A | 3/1998 | Nicholson et al. |
| 5,725,541 A | 3/1998 | Anspach, III et al. |
| 5,728,136 A | 3/1998 | Thal |
| 5,733,307 A | 3/1998 | Dinsdale |
| 5,738,685 A | 4/1998 | Halm et al. |
| 5,741,259 A | 4/1998 | Chan |
| 5,741,300 A | 4/1998 | Li |
| 5,743,914 A | 4/1998 | Skiba |
| 5,747,712 A | 5/1998 | Goto |
| 5,749,878 A | 5/1998 | Bracy et al. |
| 5,755,542 A | 5/1998 | Janusz et al. |
| 5,755,721 A | 5/1998 | Hearn |

(56) References Cited

U.S. PATENT DOCUMENTS

| | | |
|---|---|---|
| 5,766,221 A | 6/1998 | Benderev et al. |
| 5,778,623 A | 7/1998 | Powell |
| 5,782,864 A | 7/1998 | Lizardi |
| 5,782,865 A | 7/1998 | Grotz |
| 5,782,866 A | 7/1998 | Wenstrom, Jr. |
| 5,792,142 A | 8/1998 | Galitzer |
| 5,797,914 A | 8/1998 | Leibinger |
| 5,797,963 A | 8/1998 | McDevitt |
| 5,800,433 A | 9/1998 | Benzel et al. |
| 5,800,447 A | 9/1998 | Wenstrom, Jr. |
| 5,807,396 A | 9/1998 | Raveh |
| 5,808,217 A | 9/1998 | Liao |
| 5,810,824 A | 9/1998 | Chan |
| 5,810,854 A | 9/1998 | Beach |
| 5,814,051 A | 9/1998 | Wenstrom, Jr. |
| 5,814,070 A | 9/1998 | Borzone et al. |
| 5,814,071 A | 9/1998 | McDevitt et al. |
| 5,816,812 A | 10/1998 | Kownacki et al. |
| 5,824,011 A | 10/1998 | Stone et al. |
| 5,827,291 A | 10/1998 | Fucci et al. |
| 5,843,082 A | 12/1998 | Yuan et al. |
| 5,843,087 A | 12/1998 | Jensen et al. |
| 5,843,127 A | 12/1998 | Li |
| 5,851,219 A | 12/1998 | Goble et al. |
| 5,860,978 A | 1/1999 | McDevitt et al. |
| 5,860,983 A | 1/1999 | Wenstrom, Jr. |
| 5,865,559 A | 2/1999 | Yang |
| 5,868,749 A | 2/1999 | Reed |
| 5,868,762 A | 2/1999 | Cragg et al. |
| 5,868,789 A | 2/1999 | Huebner |
| 5,879,372 A | 3/1999 | Bartlett |
| 5,885,294 A | 3/1999 | Pedlick et al. |
| 5,891,146 A | 4/1999 | Simon et al. |
| 5,891,168 A | 4/1999 | Thal |
| 5,893,850 A | 4/1999 | Cachia |
| 5,899,920 A | 5/1999 | DeSatnick et al. |
| 5,902,321 A | 5/1999 | Caspari et al. |
| 5,904,704 A | 5/1999 | Goble et al. |
| 5,911,721 A | 6/1999 | Nicholson et al. |
| 5,925,048 A | 7/1999 | Ahmad et al. |
| 5,931,844 A | 8/1999 | Thompson et al. |
| 5,935,129 A | 8/1999 | McDevitt et al. |
| 5,944,739 A | 8/1999 | Zlock et al. |
| 5,948,000 A | 9/1999 | Larsen et al. |
| 5,948,001 A | 9/1999 | Larsen |
| 5,951,559 A | 9/1999 | Burkhart |
| 5,957,953 A * | 9/1999 | DiPoto ............... A61B 17/0401 606/313 |
| 5,961,538 A | 10/1999 | Pedlick et al. |
| 5,964,764 A | 10/1999 | West, Jr. et al. |
| 5,964,783 A | 10/1999 | Grafton et al. |
| 5,968,044 A | 10/1999 | Nicholson et al. |
| 5,968,078 A | 10/1999 | Grotz |
| 5,980,558 A | 11/1999 | Wiley |
| 5,989,028 A | 11/1999 | Niznick |
| 5,993,451 A | 11/1999 | Burkhart |
| 5,993,459 A | 11/1999 | Larsen et al. |
| 5,997,541 A | 12/1999 | Schenk |
| 6,007,567 A | 12/1999 | Bonutti |
| 6,013,077 A | 1/2000 | Harwin |
| 6,013,083 A | 1/2000 | Bennett |
| 6,015,252 A | 1/2000 | Peck |
| 6,019,768 A | 2/2000 | Wenstrom, Jr. et al. |
| 6,022,373 A | 2/2000 | Li |
| 6,024,758 A | 2/2000 | Thal |
| 6,027,523 A | 2/2000 | Schmieding |
| 6,030,162 A | 2/2000 | Huebner |
| 6,036,694 A | 3/2000 | Goble et al. |
| 6,042,583 A | 3/2000 | Thompson et al. |
| 6,045,554 A | 4/2000 | Grooms et al. |
| 6,045,573 A | 4/2000 | Wenstrom, Jr. et al. |
| 6,045,574 A | 4/2000 | Thal |
| 6,056,751 A | 5/2000 | Fenton, Jr. |
| 6,077,267 A | 6/2000 | Huene |
| 6,086,365 A | 7/2000 | Fields |
| 6,086,608 A | 7/2000 | Ek et al. |
| 6,090,110 A | 7/2000 | Metz-Stavenhagen |
| 6,096,041 A | 8/2000 | Gellman et al. |
| 6,099,547 A | 8/2000 | Gellman et al. |
| 6,117,161 A | 9/2000 | Li et al. |
| 6,117,162 A | 9/2000 | Schmieding et al. |
| 6,129,762 A | 10/2000 | Li |
| 6,143,017 A | 11/2000 | Thal |
| 6,149,669 A | 11/2000 | Li |
| 6,156,039 A | 12/2000 | Thal |
| 6,159,235 A | 12/2000 | Kim |
| 6,162,234 A | 12/2000 | Freedland et al. |
| 6,183,479 B1 | 2/2001 | Tormala et al. |
| 6,200,329 B1 | 3/2001 | Fung et al. |
| 6,214,031 B1 | 4/2001 | Schmieding |
| 6,221,107 B1 | 4/2001 | Steiner et al. |
| 6,231,592 B1 | 5/2001 | Bonutti et al. |
| 6,231,606 B1 | 5/2001 | Graf et al. |
| 6,280,474 B1 | 8/2001 | Cassidy et al. |
| 6,287,324 B1 | 9/2001 | Yamnitsky et al. |
| 6,319,270 B1 | 11/2001 | Grafton et al. |
| 6,319,271 B1 | 11/2001 | Schwartz et al. |
| 6,355,053 B1 | 3/2002 | Li |
| 6,368,322 B1 | 4/2002 | Luks et al. |
| 6,387,129 B2 | 5/2002 | Rieser et al. |
| 6,436,124 B1 | 8/2002 | Anderson et al. |
| 6,436,142 B1 | 8/2002 | Paes et al. |
| RE37,963 E | 1/2003 | Thal |
| 6,508,830 B2 | 1/2003 | Steiner |
| 6,511,499 B2 | 1/2003 | Schmieding et al. |
| 6,517,542 B1 | 2/2003 | Papay et al. |
| 6,517,564 B1 | 2/2003 | Grafton et al. |
| 6,520,980 B1 | 2/2003 | Foerster |
| 6,524,317 B1 | 2/2003 | Ritchart et al. |
| 6,527,772 B2 | 3/2003 | Enayati |
| 6,527,794 B1 | 3/2003 | McDevitt et al. |
| 6,527,795 B1 | 3/2003 | Lizardi |
| 6,544,281 B2 | 4/2003 | ElAttrache et al. |
| 6,551,330 B1 | 4/2003 | Bain et al. |
| 6,558,389 B2 | 5/2003 | Clark et al. |
| 6,562,044 B1 | 5/2003 | Cooper |
| 6,585,730 B1 | 7/2003 | Foerster |
| 6,610,080 B2 | 8/2003 | Morgan |
| 6,616,665 B2 | 9/2003 | Grafton et al. |
| 6,629,977 B1 | 10/2003 | Wolf |
| 6,635,074 B2 | 10/2003 | Bartlett |
| 6,641,596 B1 | 11/2003 | Lizardi |
| 6,641,597 B2 | 11/2003 | Burkhart et al. |
| 6,648,903 B1 | 11/2003 | Pierson, III |
| 6,652,561 B1 | 11/2003 | Tran |
| 6,652,563 B2 | 11/2003 | Dreyfuss |
| 6,656,183 B2 | 12/2003 | Colleran et al. |
| 6,660,008 B1 | 12/2003 | Foerster et al. |
| 6,666,877 B2 | 12/2003 | Morgan et al. |
| 6,685,728 B2 | 2/2004 | Sinnott et al. |
| 6,692,516 B2 | 2/2004 | West, Jr. et al. |
| 6,699,250 B1 | 3/2004 | Osterle et al. |
| 6,716,234 B2 | 4/2004 | Grafton et al. |
| 6,770,076 B2 | 8/2004 | Foerster |
| 6,770,084 B1 | 8/2004 | Bain et al. |
| 6,773,450 B2 | 8/2004 | Leung et al. |
| 6,780,198 B1 | 8/2004 | Gregoire et al. |
| 6,818,010 B2 | 11/2004 | Eichhorn et al. |
| 6,840,953 B2 | 1/2005 | Martinek |
| 6,857,520 B2 | 2/2005 | Salazar et al. |
| 6,875,216 B2 | 4/2005 | Wolf |
| 6,916,333 B2 | 7/2005 | Schmieding et al. |
| 6,923,824 B2 | 8/2005 | Morgan et al. |
| 6,932,834 B2 | 8/2005 | Lizardi et al. |
| 6,981,974 B2 | 1/2006 | Berger |
| 7,037,324 B2 | 5/2006 | Martinek |
| 7,083,638 B2 | 8/2006 | Foerster |
| 7,083,683 B2 | 8/2006 | Schneidereit et al. |
| 7,090,690 B2 | 8/2006 | Foerster et al. |
| 7,195,634 B2 | 3/2007 | Schmieding et al. |
| 7,204,839 B2 | 4/2007 | Dreyfuss et al. |
| 7,211,088 B2 | 5/2007 | Grafton et al. |
| 7,217,279 B2 | 5/2007 | Reese |
| 7,247,164 B1 | 7/2007 | Ritchart et al. |

(56) References Cited

U.S. PATENT DOCUMENTS

| | | | |
|---|---|---|---|
| 7,322,978 B2 | 1/2008 | West, Jr. | |
| 7,322,986 B2 | 1/2008 | Wolf | |
| 7,329,272 B2 | 2/2008 | Burkhart et al. | |
| 7,491,217 B1 | 2/2009 | Hendren et al. | |
| 7,517,357 B2 | 4/2009 | Abrams et al. | |
| 7,556,640 B2 | 7/2009 | Foerster | |
| 7,637,949 B2 | 12/2009 | Hart | |
| 7,651,495 B2 | 1/2010 | McDevitt et al. | |
| 7,695,495 B2 | 4/2010 | Dreyfuss | |
| 7,785,347 B2 | 8/2010 | Harvie et al. | |
| 7,803,173 B2 | 9/2010 | Burkhart et al. | |
| 7,883,528 B2 | 2/2011 | Grafton et al. | |
| 7,883,529 B2 | 2/2011 | Sinnott et al. | |
| 7,887,551 B2 | 2/2011 | Bojarski et al. | |
| 7,965,494 B1 | 6/2011 | Morris et al. | |
| 7,981,140 B2 | 7/2011 | Burkhart | |
| 7,993,369 B2 | 8/2011 | Dreyfuss | |
| 8,105,343 B2 | 1/2012 | White et al. | |
| 8,133,258 B2 | 3/2012 | Foerster et al. | |
| 8,137,381 B2 | 3/2012 | Foerster et al. | |
| 8,317,829 B2 | 11/2012 | Foerster et al. | |
| 8,343,186 B2 | 1/2013 | Dreyfuss et al. | |
| 8,444,672 B2 | 5/2013 | Foerster | |
| 8,623,052 B2 | 1/2014 | Dreyfuss et al. | |
| 8,764,797 B2 | 7/2014 | Dreyfuss et al. | |
| 8,801,755 B2 | 8/2014 | Dreyfuss et al. | |
| 8,821,541 B2 | 9/2014 | Dreyfuss et al. | |
| 9,179,907 B2 | 11/2015 | ElAttrache et al. | |
| 9,521,999 B2 | 12/2016 | Dreyfuss | |
| 10,595,847 B2 * | 3/2020 | Dreyfuss | A61L 17/145 |
| 11,324,493 B2 * | 5/2022 | Dreyfuss | A61B 17/0401 |
| 2001/0002439 A1 | 5/2001 | Bonutti et al. | |
| 2001/0014814 A1 | 8/2001 | Bonutti et al. | |
| 2001/0018613 A1 | 8/2001 | Huene | |
| 2001/0021862 A1 | 9/2001 | Bonutti et al. | |
| 2002/0013608 A1 | 1/2002 | ElAttrache et al. | |
| 2002/0052629 A1 | 5/2002 | Morgan et al. | |
| 2002/0087190 A1 | 7/2002 | Benavitz et al. | |
| 2002/0111653 A1 | 8/2002 | Foerster | |
| 2002/0128684 A1 | 9/2002 | Foerster | |
| 2002/0147463 A1 | 10/2002 | Martinek | |
| 2002/0188305 A1 | 12/2002 | Foerster et al. | |
| 2003/0004545 A1 | 1/2003 | Burkhart et al. | |
| 2003/0065361 A1 | 4/2003 | Dreyfuss | |
| 2003/0069604 A1 | 4/2003 | Schmieding et al. | |
| 2003/0144696 A1 | 7/2003 | Sinnott et al. | |
| 2003/0149448 A1 | 8/2003 | Foerster et al. | |
| 2003/0187444 A1 | 10/2003 | Overaker et al. | |
| 2003/0191498 A1 | 10/2003 | Foerster et al. | |
| 2003/0195563 A1 | 10/2003 | Foerster | |
| 2003/0204193 A1 | 10/2003 | Gabriel et al. | |
| 2004/0030354 A1 | 2/2004 | Leung et al. | |
| 2004/0093031 A1 | 5/2004 | Burkhart et al. | |
| 2004/0106950 A1 | 6/2004 | Grafton et al. | |
| 2004/0133239 A1 | 7/2004 | Singhatat | |
| 2004/0138683 A1 | 7/2004 | Shelton et al. | |
| 2004/0138706 A1 | 7/2004 | Abrams et al. | |
| 2004/0267316 A1 | 12/2004 | Powell et al. | |
| 2005/0107828 A1 | 5/2005 | Reese | |
| 2005/0222618 A1 | 10/2005 | Dreyfuss et al. | |
| 2005/0245932 A1 | 11/2005 | Fanton et al. | |
| 2005/0277985 A1 | 12/2005 | Wert et al. | |
| 2005/0277986 A1 | 12/2005 | Foerster et al. | |
| 2005/0283156 A1 | 12/2005 | Schmieding et al. | |
| 2005/0283158 A1 | 12/2005 | West, Jr. | |
| 2006/0004364 A1 | 1/2006 | Green et al. | |
| 2006/0074434 A1 | 4/2006 | Wenstrom et al. | |
| 2006/0079904 A1 | 4/2006 | Thal | |
| 2006/0100630 A1 | 5/2006 | West, Jr. | |
| 2006/0271060 A1 | 11/2006 | Gordon | |
| 2007/0142838 A1 | 6/2007 | Jordan | |
| 2007/0156148 A1 | 7/2007 | Fanton et al. | |
| 2007/0156149 A1 | 7/2007 | Fanton et al. | |
| 2007/0156150 A1 | 7/2007 | Fanton et al. | |
| 2007/0156176 A1 | 7/2007 | Fanton et al. | |
| 2007/0191849 A1 | 8/2007 | ElAttrache et al. | |
| 2007/0225719 A1 | 9/2007 | Stone et al. | |
| 2007/0255317 A1 | 11/2007 | Fanton et al. | |
| 2007/0260259 A1 | 11/2007 | Fanton et al. | |
| 2008/0004659 A1 | 1/2008 | Burkhart et al. | |
| 2009/0187216 A1 | 7/2009 | Schmieding et al. | |
| 2011/0015674 A1 | 1/2011 | Howard et al. | |

FOREIGN PATENT DOCUMENTS

| | | |
|---|---|---|
| EP | 0574707 A1 | 12/1993 |
| EP | 0598219 A2 | 5/1994 |
| EP | 0465910 B1 | 11/1995 |
| EP | 0686373 A1 | 12/1995 |
| EP | 0687446 A2 | 12/1995 |
| EP | 0699420 A2 | 3/1996 |
| EP | 0835640 A1 | 4/1998 |
| EP | 0951869 A1 | 10/1999 |
| EP | 1016377 | 7/2000 |
| EP | 1530951 A2 | 5/2005 |
| EP | 1762186 A3 | 3/2007 |
| EP | 1797826 B1 | 12/2009 |
| FR | 2588332 | 4/1987 |
| FR | 2622430 | 10/1987 |
| FR | 2717070 A1 | 9/1995 |
| FR | 2725615 A1 | 4/1996 |
| FR | 2738737 A1 | 3/1997 |
| GB | 651009 | 3/1951 |
| GM | 7717562 | 10/1977 |
| SU | 1034734 | 8/1983 |
| SU | 1600713 A1 | 10/1990 |
| WO | 94/28811 A1 | 12/1994 |
| WO | 95/22930 A1 | 8/1995 |
| WO | 96/14798 A1 | 5/1996 |
| WO | 96/41574 A2 | 12/1996 |
| WO | 98/26717 A1 | 6/1998 |
| WO | 99/37217 | 7/1999 |
| WO | 99/53844 A1 | 10/1999 |
| WO | 01/10312 A1 | 2/2001 |
| WO | 02/21998 A2 | 3/2002 |
| WO | 2009/055075 | 4/2009 |

OTHER PUBLICATIONS

Figure 2 diagram. Slocum, Apr. 27, 2017. Slocum Exhibit 8 from *Smith & Nephew* v. *Arthrex*, Case IPR 2016-00918.

Figure 1 Diagram. Slocum, Apr. 27, 2017. Slocum Exhibit 9 from *Smith & Nephew* v. *Arthrex*, Case IPR 2016-00918.

Figure 3 Diagram. Slocum, Apr. 27, 2017. Slocum Exhibit 10 from *Smith & Nephew* v. *Arthrex*, Case IPR 2016-00918.

Screenshot of file list from Exhibit 1173. Arthrex Exhibit 2045, *Smith & Nephew* v. *Arthrex*. Case IPR2016-00918.

Rotated view of screw cross section with female and male configuration from Exhibit 1173. Arthrex Exhibit 2046, *Smith & Nephew* v. *Arthrex* Case IPR2016-00918.

Screenshot of file list from Exhibit 1174. Arthrex Exhibit 2047. *Smith & Nephew* v. *Arthrex* Case IPR2016-00918.

Image of PDF "drivers in hexagons 0.36 mmslot.PDF" Arthrex Exhibit 2048. *Smith & Nephew* v. *Arthrex*. Case IPR2016-00918.

Annotated screenshot of file "drivers in hexagons.SLDASM" from exhibit 1174. Arthrex Exhibit 2049. *Smith & Nephew* v. *Arthrex* Case IPR2016-00918.

Rotated view of "drivers in hexagons. SLDASM" from exhibit 1174. Arthrex Exhibit 2050. *Smith & Nephew* v. *Arthrex* Case IPR2016-00918.

Transcript of Deposition of Alexander H. Slocum Ph.D., *Smith & Nephew, Inc., et al.,* v. *Arthrex, Inc.,* May 17, 2017, Boston, MA.

"Patent Owner's Oral Argument for Claims 10 and 11 of U.S. Pat. No. 8,821,541" Arthrex Exhibit 2053. *Smith & Nephew* v. *Arthrex* Case IPR2016-00918.

510(k) Summary of Safety and Effectiveness, DePuy Inc, Feb. 6, 1997.

Abrams, Jeffrey S., et al., Arthroscopic Rotator Cuff Surgery, A Practical Approach to Management, 2008.

(56) References Cited

OTHER PUBLICATIONS

Arthrex is Reaching New Heights in Rotator Cuff Repair, Arthrex, Inc., 2007.
Barber, M.D., F. Alan, Biodegradable Shoulder Anchors Have Unique Modes of Failure, Arthroscopy: The Journal pf Arthroscopic and Related Surgery, vol. 23, No. 3 (Mar.), 2007, pp. 316-320.
Barber, M.D., F. Alan et al., Biomechanical Analysis of Pullout Strength of Rotator Cuff and Glenoid Anchors: 2011 Update, Arthroscopy: The Journal of Arthroscopic and Related Surgery, vol. 27, No. 7 (Jul.), 2011; pp. 895-905.
Barber, M.D., F. Alan et al., The In Vivo Histology of an Absorbable Suture Anchor: A Preliminary Report, Arthroscopy: The Journal of Arthroscopic and Related Surgery, vol. 11, No. 1 (Feb.), 1995, pp. 77-81.
Barber, M.D., F. Alan et al., Suture Anchor Failure Strength—An In Vivo Study, Arthroscopy: The Journal of Arthroscopic and Related Surgery, vol. 9, No. 6, 1993., pp. 647-652.
Barber, M.D., F. Alan et al., Suture Anchor Strength Revisited, Arthroscopy: The Journal of Arthroscopic and Related Surgery, vol. 12, No. 1 (Feb.), 1996: pp. 32-38.
Barber, M.D., F. Alan et al., Suture Anchors—Update 1999, Arthroscopy: The Journal of Arthroscopic and Related Surgery, vol. 15, No. 7, (Oct.), 1999: pp. 719-725.
Barber, M.D., F. Alan et al., The Ultimate Strength of Suture Anchors, Arthroscopy: The Journal of Arthroscopic and Related Surgery, vol. 11, No. 1 (Feb.), 1995: pp. 21-28.
Barber, M.D., F. Alan et al., Sutures and Suture Anchors: Update 2003, Arthroscopy: The Journal of Arthroscopic and Related Surgery, vol. 19, No. 9 (Nov.), 2003: pp. 985-990.
Barber, M.D., F. Alan et al., Sutures and Suture Anchors: Update 2006, Arthroscopy: The Journal of Arthroscopic and Related Surgery, vol. 22, No. 10 (Oct.), 2006: pp. 1063-1069.
Barber, M.D., F. Alan et al., Suture Anchor Materials, Eyelets, and Designs: Update 2008, Arthroscopy: The Journal of Arthroscopic and Related Surgery, vol. 24, No. 8 (Aug.), 2008: pp. 859-867.
Bioknotless™ Anchor, The First Absorbable Knotless Suture Anchor, Mitek® Products, 2001.
Burkhart, Stephen S. et al., Chapter 4, Current Concepts of Rotator Cuff Repair, pp. 81-88.
Burkhart M.D., Stephen S. et al., Cyclic Loading of Anchor-Based Rotator Cuff Repairs: Confirmation of the Tension Overload Phenomenon and Comparison of Suture Anchor Fixation With Transosseous Fixation, Arthroscopy: The Journal of Arthroscopic and Related Surgery, vol. 13, No. 6 (Dec.), 1997: pp. 720-724.
Burkhart, M.D., Stephen S., The Deadman Theory of Suture Anchors: Observations Along a South Texas Fence Line, Arthroscopy: The Journal of Arthroscopic and Related Surgery, vol. 11, No. 1 (Feb.), 1995: pp. 119-123.
Burkhart M.D., Stephen S., Partial Repair of Irreparable Rotator Cuff Tears, Arthroscopy: The Journal of Arthroscopic and Related Surgery, vol. 10, No. 4, 1994, pp. 363-370.
Burkhart M.D., Stephen S., Slap Lesions in Association with Complete Tears of the Long Head of the Biceps Tendon: A Report of Two Cases, Arthroscopy: The Journal of Arthroscopic and Related Surgery, vol. 8, No. 1, 1992, pp. 31-35.
Craft M.D., David V et al., Fixation strength of rotator cuff repairs with suture anchors and the transosseous suture technique, Journal of Shoulder and Elbow Surgery Board of Trustees, 1996, pp. 32-40.
Denard, M.D., Patrick J., The Evolution of Suture Anchors in Arthroscopic Rotator Cuff Repair, Arthroscopy: The Journal of Arthroscopic and Related Surgery, vol. 29, No. 9 (Sep.), 2013: pp. 1589-1595.
Gerber, Christian et al., Mechanical Strength of Repairs of the Rotator Cuff, The Journal of Bone and Joint Surgery, vol. 76-B, No. 3, May 1994, pp. 371-380.
Harryman, II, M.D., Douglas T., Repairs of the Rotator Cuff, Correlation of Functional Results with Integrity of the Cuff, The Journal of Bone and Joint Surgery, vol. 73-A, No. 7, Aug. 1991, pp. 982-989.

Hecker, Aaron T. et al., Pull-out strength of suture anchors for rotator cuff and Bankart lesion repairs, The American Journal of Sports Medicine, vol. 21, No. 6, 1993, pp. 874-879.
Johnson, MD, FRCS, Donald H. et al., Chapter 20: Thermal Treatment, Sutures, Knots, and Bone Anchors, Practical Orthopaedic Sports Medicine and Arthroscopy, 2007, pp. 303-305.
Lovald Ph.D, Scott et al., Chapter 15: Applications and Polyetheretherketone in Trauma, Arthroscopy, and Cranial Defect Repair, PEEK Biomaterials Handbook, 2012, pp. 243-260.
Ma, Richard et al., Arthroscopic rotator cuff repair: suture anchor properties, modes of failure and technical considerations, Expert Rev. Med. Devices 8(3), 2011, pp. 377-387.
Meyer, M.D., Dominik C., Failure of Suture Material at Suture Anchor Eyelets, Arthroscopy: The Journal of Arthroscopic and Related Surgery, vol. 18, No. 9 (Nov.-Dec.), 2002: pp. 1013-1019.
Millstein, M.D., Eric S. et al., Instructional Course 302: Arthroscopic Management of Partial, Full-Thickness, and Complex Rotator Cuff Tears: Indications, Techniques, and Complications, Arthroscopy: The Journal of Arthroscopic and Related Surgery, vol. 19, No. 10 (Dec., Suppl 1), 2003: pp. 189-199.
Ono, Ichiro et al., Evaluation of a high density polyethylene fixing system for hydroxyapatite ceramic implants, Biomaterials 21 (2000), pp. 143-151.
Pietschmann, M.D., Matthias F., Biomechanical Stability of Knotless Suture Anchors Used in Rotator Cuff Repair in Healthy and Osteopenic Bone, Arthroscopy: The Journal of Arthroscopic and Related Surgery, vol. 26, No. 8 (Aug.), 2010: pp. 1035-1044.
Reed, Stephen C., Full Thickness Rotator Cuff Tears, A Biomechanical Comparison of Suture Versus Bone Anchor Techniques, The American Journal of Sports Medicine, vol. 24, No. 1, 1996: pp. 46-48.
Richmond, John C., Modification of the Bankart reconstruction with a suture anchor, Report of a new technique, The American Journal of Sports Medicine, vol. 19, No. 4, 1991: pp. 343-346.
Rupp, M.D., Stefan, Fatigue Testing of Suture Anchors, The American Journal of Sports Medicine, vol. 30, No. 2, 2002, pp. 239-247.
Snyder, M.D., Stephen J., Technique of Arthroscopic Rotator Cuff Repair Using Implantable 4-MM REVO Suture Anchors, Suture Shuttle Relays, and No. 2 Nonabsorbable Mattress Sutures, The Rotator Cuff, Part II, Orthopedic Clinics of North America, vol. 28, No. 2, Apr. 1997, pp. 267-275.
Weideman, Ph.D., Carol A., 510(k) Summary of Safety and Effectiveness, Mar. 21, 1997.
Wolf, M.D., Eugene M., Arthroscopic Bankart Repair Using Suture Anchors, Operative Techniques in Orthopaedics, vol. 1, No. 2 (Apr.), 1991: pp. 184-191.
Wolf, M.D., Eugene M., Arthroscopic Capsulolabral Repair Using Suture Anchors, Shoulder Arthroscopy and Related Surgery, Orthopedic Clinics of North America, vol. 24, No. 1, Jan. 1993, pp. 59-69.
510(K) Summary for Arthrex, Inc.'s Bio-Interference Screw, Jul. 9, 1997.
Ahmad MD, Christopher S., Arthroscopic biceps tenodesis, Orthopedi Clinics of North America, 2003, pp. 499-506.
An Absorbable Interference Screw . . . the difference is Acufex, Acufex, Smith & Nephew Endoscopy, 1995.
Arthrex Corkscrew™ Suture Anchors, 1996.
Arthrex Surgical Techniques, https://web.archive.org/web/19981206111626/http://www.arthrex.com/Procedures.htm; Dec. 6, 1998.
Welcome to Arthrex, https://web.archive.org/web/19981111190428/http://www.arthrex.com/; Nov. 11, 1998.
Bach, Jr. M.D., Bernard R., Observations on Interference Screw Morphologies, Arthroscopy: The Journal of Arthroscopic and Related Surgery, vol. 16, No. 5 (Jul.-Aug.), 2000: E10, pp. 1-6.
Barber, M.D., F. Alan et al., Preliminary Results of an Absorbably Interference Screw, Arthroscopy: The Journal of Arthroscopic and Related Surgery, vol. 11, No. 5 (Oct.), 1995: pp. 537-548.
Bellemans, M.D.,Ph.D, Johan, A Modified Technique for Tibial Interference Screw Fixation of Hamstring Anterior Cruciate Ligament Grafts, Arthroscopy: The Journal of Arthroscopic and Related Surgery, vol. 15, No. 6 (Sep.), 1999: pp. 669-671.
Benterud, Jan G. et al., Implant holding power of the femoral head, Acta Orthop Scand 119; 63(1): pp. 47-49.

(56) References Cited

OTHER PUBLICATIONS

Caborn, M.D., David N. M. et al., Quadrupled Semitendinosus-Gracilis Autograft Fixation in the Femoral Tunnel: A Comparison Between a Metal and a Bioabsorbably Interference Screw, Arthroscopy: The Journal of Arthroscopic and Related Surgery, vol. 14, No. 3 (Apr.), 1998: pp. 241-245.
Chapman, J.R. et al., Factors Affecting the Pullout Strength of Cancellous Bone Screws, Journal of Biomechanical Enginnering, Aug. 1996, vol. 11, pp. 391-398.
Corry, MD, FRCS(Orth), Ian S. et al., Arthroscopic Reconstruction of the Anterior Cruciate Ligament, The American Journal of Sports Medicine, vol. 27, No. 3, 1999, pp. 444-454.
The products you Need . . . The convenience you want . . . and the value you deserve., Acufex Microsurgical, Inc., 1994.
Lambert, M.D., Kenneth L., Vascularized Patellar Tendon Graft with Rigid Internal Fixation for Anterior Cruciate Ligament Insufficiency, Clinical Orthopaedics and Related Research, Jan.-Feb. 1983, pp. 85-89.
Lo, MD, Ian K.Y. et al., Arthroscopic Biceps Tenodesis: Indications and Technique, Operative Techniques in Sports Medicine, vol. 10, No. 2 (Apr.), 2002: pp. 105-112.
Mazzocca, MD, A.D. et al., Single Incision Technique Using an Interference Screw for the Repair of Distal Biceps Tendon Ruptures, Operative Techniques in Sports Medicine, vol. 11, No. 1 (Jan.), 2003: pp. 36-41.
Pearls of Wisdom, https://web.archive.org/web/19981201194509/http://www.arthrex.com/pearls.htm, Dec. 1, 1998.
Perren, SM et al., Technical and biomechanical aspects of screws used for bone surgery, International Journal of Orthopaedic Trauma 1992; 2: pp. 31-48.
Rehnberg, Lars et al., Uppsala Screw Fixation Versus the von Bahr Technique in Displaced Cervical Hip Fractures: Preliminary Report, Journal of Orthopaedic Trauma, vol. 3, No. 1, 1989, pp. 48-52.
Richards, MD, David P. et al., Arthroscopic Biceps Tenodesis with Interference Screw Fixation: The Lateral Decubitus Position, Operative Techniques in Sports Medicine, vol. 11, No. 1 (Jan.), 2003; pp. 15-23.
Rupp, MD, Stefan et al., Fixation Strength of a Biodegradable Interference Screw and a Press-Fit Technique in Anterior Cruciate Ligament Reconstruction With a BPTB Graft, Arthroscopy: The Journal of Arthroscopic and Related Surgery, vol. 13, No. 1 (Feb.), 1997: pp. 61-65.
Caborn, M.D., David et al., Arthroscopic Repair of a Bankart Lesion Using TAG® Suture Anchors, Smith & Nephew Endoscopy, 1996.
Smith & Nephew, 1997 Products Catalog.
Tencer, Allen F. et al., Biomechanics of Cannulated and Noncannulated Screws, Cannulated Screw Fixation, 1996, pp. 15-40.
McGuire, MD, David A., The BioScrew® Fixation System, Linvatec, 1995.
Uhl, MD, Richard L., The Biomechanice of Screws, Orthopaedic Review, vol. XVIII, No. 12, Dec. 1989, pp. 1302-1307.
Using the T-Fix, Acufex Microsurgical, Inc., 1995.
Von Bahr, Viktor et al., Osteosynthesis of Femoral Neck Fracture Using Screws, Acta Chir Scand 140; pp. 277-282, 1974.
Weiler, MD, Andreas et al., Biodegradable Interference Screw Fixation Exhibits Pull-Out Force and Stiffness Similar to Titanium Screws*, The American Journal of Sports Medicine, vol. 26, No. 1, 1998, pp. 119-128.
Weiler, MD, Andreas et al., Hamstring Tendon Fixation Using Interference Screws: A Biomechanical Study in Calf Tibial Bone, Arthroscopy: The Journal of Arthroscopic and Related Surgery, vol. 14, No. 1 (Jan.-Feb.), 1998: pp. 29-37.
510(K) Summary for Arthrex, Inc.'s FASTak Suture Anchor, Apr. 18, 1996.
Stadelmaier, DO, Denise M. et al., "Cyclic Pull-Out Strength of Hamstring Tendon Graft Fixation with Soft Tissue Interference Screws" The American Journal of Sports Medicine, vol. 27, No. 6, 1999, pp. 778-783.
Kurosaka, MD, Masahiro et al., "A biomechanical comparison of different surgical techniques of graft fixation in anterior cruciate ligament reconstruction" The American Journal of Sports Medicine, vol. 15, No. 3, 1987, pp. 225-229.
U.S. Food and Drug Administration Guidance: Use of International Standard ISO-10993, 'Biological Evaluation of Medical Devices Part 1: Evaluation and Testing', 1995.
Hayes, "Biomechanics of Cortical and Trabecular Bone: Implications for Assessment of Fracture Risk," Basic Orthopaedic Biomechanics, pp. 93-142 (1991).
Petition for Inter Partes Review of U.S. Pat. No. 8,343,186, filed in the United States Patent and Trademark Office on Jan. 27, 2016, Case No. IPR2016-00505.
Petition for Inter Partes Review of U.S. Pat. No. 8,623,052, filed in the United States Patent and Trademark Office on Jan. 27, 2016, Case No. IPR2016-00506.
Petition for Inter Partes Review of U.S. Pat. No. 8,801,755, filed in the United States Patent and Trademark Office on Jan. 27, 2016, Case No. IPR2016-00507.
Petition for Inter Partes Review of U.S. Pat. No. 8,801,755, filed in the United States Patent and Trademark Office on Jan. 27, 2016, Case No. IPR2016-00508.
Defendants' Invalidity Contentions and Production of Documents Pursuant to Patent Rules 3-3 and 3-4(B), *Arthrex, Inc.* v. *Smith & Nephew, Inc. and Arthrocare Corp.*, Civil Action No. 2:15-CV-1047-RSP; filed Nov. 18, 2015.
Corkscrew Product Sheet from Arthrex Catalog 1998-1999.
Oberg et al., "Screw Threads" Machinery's Handbook: A Reference Book for the Mechanical Engineer, Manufacturing Engineer, Draftsman, Toolmaker, and Machinist, pp. 1633, Industrial Press Inc., New York, NY (1996).
Goradia, M.D., Vipool K. et al., "Cyclic Loading of Rotator Cuff Repairs: A Comparison of Bioabsorbable Tacks With Metal Suture Anchors and Transosseous Sutures" Arthroscopy: The Journal of Arthroscopic and Related Surgery, vol. 17, No. 4 (Apr.), 2001: pp. 360-364.
Goble, M.D., E. Marlowe, "The Development of Suture Anchors for Use in Soft Tissue Fixation to Bone" The American Journal of Sports Medicine, vol. 22, No. 2, 1994.
Lajtai, G. et al., Shoulder Arthroscopy and MRI Techniques, 2003.
Asnis et al., "Cancellous Bone Screw Design and Holding Power," 62nd Annual Meeting of American Academy of Orthopaedic Surgeons, pp. 465-466 (Feb. 1995).
Decoster, Thomas A. et al., "Optimizing Bone Screw Pullout Force," Journal of Orthopaedic Trauma, vol. 4, No. 2, pp. 169-174, 1990.
Orthopedics, Feb. 1997, vol. 20, No. 2, pp. 160, 174 and 182.
Goble, E. Marlowe et al., The Development of Suture Anchors for Use in Soft Tissue Fixation to Bone, The American Journal of Sports Medicine, vol. 22, No. 2, 1994, pp. 236-239.
Chang, D.P.M., Thomas J., Soft Tissue Anchors: An Update, Chapter 50, pp. 301-305.
Labral Repair with Statak® Suture Anchors, Surgical Techniques, Arthroscopic & Open, Zimmer, 97-2344-03, 1996.
Statak™ Soft Tissue Attachment Device Technique Guide, Surgical Techniques, Common Foot Procedures, Zimmer, 97-2344-58 Rev. 1, 1995.
Rotator Cuff Repair with Statak® Suture Anchors Technique Guide, Surgical Techniques, Arthroscopic & Open, Zimmer, 97-2344-04, 1996.
Pederson, DPM, Bradley et al., Mitek® Anchor System: A New Technique for Tenodesis and Ligamentous Repair of the Foot and Ankle, The Journal of Foot Surgery, vol. 30, No. 1, 1991, pp. 48-51.
Yu, DPM, Gerard V. et al., Soft Tissue Anchors, 1992, pp. 120-125.
IMF Screw Set for Intermaxillary Fixation, Synthes® Maxillofacial, 2001.
Stryker Leibinger, IMF Screw System for Intermaxillary Fixation Brochure.
Arthur, DMD, Gregory et al., A Simplified Technique of Maxillomandibular Fixation, American Association of Oral and Maxillofacial Surgeons, 1989, p. 1234.
Busch, M.D., D.D.S, Richard F., Maxillomandibular Fixation Utilizing Cortical Bone Screws, Correspondence and Brief Communications, p. 262.

(56) References Cited

OTHER PUBLICATIONS

Karlis, D.M.D., Vasiliki et al., Reply, Plastic and Reconstructive Surgery, Apr. 1998, p. 1414.
Karlis, D.M.D, Vasiliki et al., An Alternative to Arch-Bar Maxillomandibular Fixation, Ideas and Innovations, vol. 99, No. 6, 1996, pp. 1758-1759.
Martin Fami Screws Brochure.
Mondeal IMF Quick-Fix System Brochure.
"The AutoCuff™ System," Opus Medical, 2003.
Apreleva, Ph.D. et al., Maria, Rotator Cuff Tears: The Effect of the Reconstruction Method on Three-Dimensional Repair Site Area, Arthroscopy: The Journal of Arthroscopic and Related Surgery, vol. 18, No. 5 (May-Jun.), 2002: pp. 519-526.
George, MD, Michael S. et al., Suture Anchors in Arthroscopic Rotator Cuff Repair, Operative Techniques in Sports Medicine, 2004, pp. 210-214.
Millett, MD, Peter J., Mattress Double Anchor Footprint Repair: A Novel, Arthroscopic Rotator Cuff Repair Technique, Arthroscopy: The Journal of Arthroscopic and Related Surgery, vol. 20, No. 8 (Oct.), 2004: pp. 875-879.
Robbe, MD, Rudy et al., Knotless Suture-Based Anchors, Operative Techniques in Sports Medicine, 2004, pp. 221-224.
Thal, MD, Raymond, Knotless Suture Anchor, Arthroscopic Bankart Repair Without Tying Knots, Clinical Orthopaedics and Related Research, No. 390, 2001, pp. 42-51.
Waltrip, Robert L., Rotator Cuff Repair: A Biomechanical Comparison of Three Techniques, The American Journal of Sports Medicine, vol. 31, No. 4, 2003., pp. 493-497.
Yian, M.D., Edward et al., Arthroscopic Repair of SLAP Lesions With a Bioknotless Suture Anchor, Arthroscopy: The Journal of Arthroscopic and Related Surgery, vol. 20, No. 5, (May-Jun.), 2004: pp. 547-551.
Zumstein, M.D., Matthias, In Vitro Comparison of Standard and Knotless Metal Suture Anchors, Arthroscopy: The Journal of Arthroscopic and Related Surgery, vol. 20, No. 5 (May-Jun.), 2004: pp. 517-520.
Judgment—Granting Request for Adverse Judgment Before Institution of Trial 37 C.F.R. § 42.73(b) dated Sep. 21, 2016, Case IPR2016-00917, from the United States Patent and Trademark Office.
Decision—Granting Institution of Inter Partes Review 37 C.F.R. § 42.108 dated Oct. 17, 2016, Case IPR2016-00918, from the United States Patent and Trademark Office.
Decision—Institution of Inter Partes Review of U.S. Pat. No. 8,343,186 dated Jul. 27, 2016, Case IPR2016-00505, from the United States Patent and Trademark Office.
Decision—Institution of Inter Partes Review of U.S. Pat. No. 8,623,052 dated Aug. 2, 2016, Case IPR2016-00506, from the United States Patent and Trademark Office.
Decision—Institution of Inter Partes Review of U.S. Pat. No. 8,801,755 dated Jul. 27, 2016, Case IPR2016-00507, from the United States Patent and Trademark Office.
Decision—Institution of Inter Partes Review of U.S. Pat. No. 8,801,755 dated Jul. 27, 2016, Case IPR2016-00508, from the United States Patent and Trademark Office.
Petition for Inter Partes Review of U.S. Pat. No. 8,821,541, filed in the United States Patent and Trademark Office on Apr. 19, 2016, Case No. IPR2016-00918.
Petition for Inter Partes Review of U.S. Pat. No. 8,821,541, filed in the United States Patent and Trademark Office on Apr. 19, 2016, Case No. IPR2016-00917.
European Search Report for EP Application No. 05102676.3 dated Aug. 29, 2005.
"Bone Screw Technical Information," Richards Manufacturing Company, Inc. Tech. Publ. 1980, pp. 1-14.
"Implants for Surgery-Metal Bone Screws With Hexagonal Drive Connection, Spherical Under-Surface of Head, Asymmetrical Thread-Dimensions," International Standard ISO 5834, 1991(E), pp. 1-10.
Linvatec Revo Cancellous Screw Advertisement, 1993.

R.M. Altieri Mitek Surgical Products announces fourth-quarter and year-end results, Business Wire (Feb. 24, 1995).
Rupp et al., "Fatigue Testing of Suture Anchors," The American Journal of Sports Medicine, Mar. 2002, vol. 30, No. 2, pp. 239-247.
Laws, "Suturing Techniques," Principles of Laparoscopic Surgery, 1995, pp. 35-45.
File History of U.S. Pat. No. 8,821,541.
Declaration of Mark A. Ritchart. In re U.S. Pat. No. 8,821,541, Claims 10 and 11. Executed Apr. 19, 2016. pp. 1-158.
CV of Mark A. Ritchart, 951-551-0162. pp. 1-3.
Dreyfuss, Utility Patent Application Transmittal for U.S. Appl. No. 11/097,568, Fully Threaded Suture Anchor With Transverse Anchor Pin, pp. 1-29.
Dreyfuss, Utility Patent Application Transmittal for U.S. Appl. No. 10/083,568, Fully Threaded Suture Anchor with Transverse Anchor Pin, pp. 1-29.
Grafton et al., Utility Patent Application Transmittal for U.S. Appl. No. 09/495,816, Bioabsorbable Tissue Tack With Oval-Shaped Head and Method of Tissue Fixation Using Same, p. 1-9.
Dreyfuss, Utility Patent Application Transmittal for U.S. Appl. No. 11/224,060, Fully-Threaded Bioabsorbable Suture Anchor, pp. 1-51.
Provisional Application for Patent Cover Sheet for U.S. Appl. No. 60/271,414, filed Feb. 27, 2001, pp. 1-7.
Provisional Application for Patent Cover Sheet for U.S. Appl. No. 60/118,228, filed Feb. 2, 1999, pp. 1-11.
Provisional Application for Patent Cover Sheet for U.S. Appl. No. 60/125,781, filed Mar. 23, 1999, pp. 1-15.
Provisional Application for Patent Cover Sheet for U.S. Appl. No. 60/715,614, filed Sep. 12, 2005, pp. 1-10.
The American Heritage College Dictionary, Third Edition, 2000, pp. 227, 956, 998.
Appendix B. Exhibit 120 to "Plaintiff Arthrex, Inc.'s Disclosures of Asserted Claims and Infringement Contentions as to Defendants Smith & Nephew, Inc., and Arthrocare Corp., and Identification of Document Production Accompanying Disclosure," Civil Action No. 2:15-CV-1047-JRG (E.D. Tex.).
Declaration of Nathan R. Speed in Support of Motion for Admission Pro Hac Vice, May 31, 2016.
Arthrex "About Us" webpage, 2016.
Erin Carlyle, Meet Reinhold Schmieding, The Florida Medical Device Billionaire You've Never Heard of, Forbes.com LLC, Aug. 6, 2013, pp. 1-3.
Random House Webster's College Dictionary, Second Edition, 1999. p. 154-155, 210-211, 252-253, 350-351, 363, 382-383, 494-497, 680-681, 686-687, 778-779, 782-783, 824-825, 882-883, 964-965, 1064-1065, 1134-1135, 1296, 1312-1313.
The American Heritage College Dictionary, Fourth Edition, May 24, 2004, pp. 174-175.
Erin McKean, The New Oxford American Dictionary, Second Edition, May 17, 2005, pp. 876.
John McCormick, ArthroCare Closes Opus Medical Acquisition, HealthPointCapital, Nov. 22, 2004, New York, NY, pp. 1-3.
Arthrocare Corporation, et al., Agreement and Plan of Merger Sep. 3, 2004, pp. 1-85.
Maurice Waite, et al., Oxford Paperback Dictionary and Thesaurus, Third Edition, 2009, pp. 966.
Erik Oberg, et al., Machinery's Handbook, 24th Edition, Industrial Press Inc., New York, 1992, pp. 1524.
Declaration of Ken Gall, PhD, *Smith & Nephew, Inc., et al.,* v. *Arthrex, Inc.,* Case No. IPR2016-00918, U.S. Pat. No. 8,821,541, Jan. 14, 2017, pp. 1-184.
Deposition of Mark A. Ritchart, *Smith & Nephew, Inc., et al.,* v. *Arthrex, Inc.,* Case No. IPR2016-00918, U.S. Pat. No. 8,821,541, Nov. 29, 2016.
Reporter's Transcript of Jury Trial, *Arthrex, Inc.* v. *Smith & Nephew, et al.,* Dec. 6, 2016, vol. 3, pp. 441-776.
Arthrex Covered Products Chart. https://www.arthrex.com/products/AR-1927PSF-45.
Copying Products Charts and Supporting Materials. Arthrex Exhibit 2014 from *Smith & Nephew* V. *Arthrex,* Case IPR2016-00918.
510(k) Summary, 510(k) No. K110781, ArthroCare Corporation Spartan PEEK Suture Implant System, May 27, 2011.

(56) References Cited

OTHER PUBLICATIONS

Ervin, Corinne. "AthroCare received FDA Clearance for Spartan 6.5 Needled Suture Implant." Business Wire. Jun. 6, 2011.
Cayenne Medical, Inc., Cayenne Medical Launches Quattro Shoulder System for Rotator Cuff and Labral Repair, Jul. 10, 2012, Scottsdale, Arizona, pp. 1-3.
510(k) Summary, 510(k) No. K101100, ConMed Linvatec CrossFT BC Suture Anchor, Aug. 26, 2010.
510(k) Summary, Section 2, 510(k) No. K082282, Healix Ti Anchor, Nov. 7, 2018.
510(k) Premarket Notification, 510(k) No. K120942, FDA, Silver Spring, MD, pp. 1-2.
510(k) Summary of Safety and Effectiveness, 510(k) No. K100159. Smith & Nephew Twinfix Ultra PK Suture Anchor. Apr. 19, 2010.
510(k) Summary of Safety and Effectiveness, 510(k) No. K083268. Tornier Insite. Feb. 12, 2009.
Arthrocare Corp. Speed Screw figures. Arthrex Exhibit 2023 from *Smith & Nephew* v. *Arthrex*, Case IPR 2016-00918.
Declaration of Christopher A. Vellturo, Ph.D., Jan. 13, 2017, pp. 1-18. (Unredacted).
Declaration of Christopher A. Vellturo, Ph.D., Jan. 13, 2017, pp. 1-18. Redacted.
Modified Protective Order—Redlines Relative to Board's Standing Protective Order. *Smith & Nephew, Inc., et al*, v. *Arthrex, Inc.*, Case No. IPR2016-00918, U.S. Pat. No. 8,821,541, pp. 1-9.
Modified Protective Order—Clean. *Smith & Nephew, Inc., et al*, v. *Arthrex, Inc.*, Case No. IPR2016-00918, U.S. Pat. No. 8,821,541, pp. 1-9.
Declaration of Christopher Holter, Jan. 13, 2017, pp. 1-11. Redacted.
Declaration of Christopher Holter, Jan. 13, 2017, pp. 1-11. Unredacted.
Roy S. Payne, Judgment, *Arthrex, Inc.* v. *Smith & Nephew, Inc., et al.*, Case No. 2:15-cv-01047-RSP, Document No. 299, Dec. 12, 2016.
Declaration of Jessica Zilberberg, *Smith & Nephew, Inc., et al.*, v. *Arthrex, Inc.*, Case No. IPR2016-00918, U.S. Pat. No. 8,821,541, Jan. 13, 2017.
Kathryn E. Smith, et al., Use of 3D Printed Bone Plate in Novel Technique to Surgically Correct Hallux Valgus Deformities, Techniques of Orthopedics, vol. 00, No. 00, 2016., pp. 1-9.
Atlas of Stress-Strain Curves, Second Edition, The materials Information Society, 2002.
CAD Diagram—Slocum, Apr. 27, 2017. Slocum Exhibit 4.
Handwritten Formula by Slocum. Apr. 27, 2017. Slocum Exhibit 5 from *Smith & Nephew* v. *Arthrex*, Case IPR2016-00918.
Diagram Showing Cortical Layer by Slocum. Apr. 27, 2017. Slocum Exhibit 6 from *Smith & Nephew* v. *Arthrex*, Case IPR 2016-00918.
Bacilla M.D., Phillip, "Arthroscopic Bankart Repair in a High Demand Patient Population", Arthroscopy: The Journal of Arthroscopic and Related Surgery, vol. 13, No. 1, Feb. 1997, pp. 51-60.
All Soft Tissue Anchors Are Not Created Equal . . . , Orthopaedic Biosystems Ltd., Inc., 1996.
M3-X Extremity Fixation System Just Drill and Drive, Osteomed Corporation, 1994.
Mitek Gll Anchor™ System, Instrument Guide/Ordering Information, Mitek® Surgical Products, Inc., 1994.
Mitek Gll Anchor™ System, Instrument Guide/Ordering Information, 1994.
Bradley M.D., James P., Labral Repair With Statak, Linvatec, 1994.
Your open techniques work . . . Let Our Arthroscopic Tools Work for You, Innovasive® Devices, Inc., 1995.
Snyder, M.D., Stephen, The Mini-Reva Labral Repair System, Linvatec, 1994.
Higgins, MD et al., Laurence D., Arthroscopic Bankart Repair, Operative Technique and Surgical Pitfalls, Clinics in Sports Medicine, vol. 19, No. 1, Jan. 2000, pp. 49-62.
Cole, MD, MBA et al., Brian J., Arthroscopic Shoulder Stabilization With Suture Anchors: Technique, Technology, and Pitfalls, Clinical Orthopaedics and Related Research, vol. 390, Sep. 2001, pp. 17-30.
Barber, M.D., F. Alan et al., Internal Fixation Strength of Suture Anchors—Update 1997, Arthroscopy: The Journal of Arthroscopic and Related Surgery, vol. 13, No. 3 (Jun.), 1997, pp. 355-362.

\* cited by examiner

FULLY-THREADED BIOABSORBABLE SUTURE ANCHOR

REFERENCE TO RELATED APPLICATION

This application is a continuation of U.S. patent application Ser. No. 16/784,612 filed on Feb. 7, 2020, now U.S. Pat. No. 11,324,493 granted May 10, 2022, which is a continuation of U.S. patent application Ser. No. 15/382,855 filed on Dec. 19, 2016, now U.S. Pat. No. 10,595,847 granted Mar. 24, 2020, which is a continuation of U.S. patent application Ser. No. 11/224,060 filed on Sep. 13, 2005, now U.S. Pat. No. 9,521,999 granted Dec. 20, 2016.

FIELD

The present invention relates to an apparatus and method for anchoring surgical suture to bone. More specifically, the present invention relates to arthroscopic apparatus and methods for anchoring suture to bone using a fully-threaded bioabsorbable suture anchor having a loop inserted into the suture anchor.

BACKGROUND

When soft tissue tears away from bone, reattachment becomes necessary. Various devices, including sutures alone, screws, staples, wedges, and plugs have been used in the prior art to secure soft tissue to bone. Recently, various types of threaded suture anchors have been developed for this purpose. Some threaded suture anchors are designed to be inserted into a pre-drilled hole. Other suture anchors are self-tapping.

Problems can arise if the structure for attaching the suture fails, allowing the suture to become detached from the anchor. Also, the suture often is exposed to abrasion or cutting by sharp or rough areas along the walls of the bone canal into which the anchor is inserted.

Further, the prior art suture anchors having eyelets extending from the proximal ends require countersinking of the eyelet below the bone surface to avoid having the patient's tissue abrade against the exposed eyelet. As a result, suture attached to the eyelet is vulnerable to abrasion by the bony rim of the countersunk hole into which the suture anchor is installed. In addition, in biodegradable prior art devices, the eyelet can degrade rapidly, causing the suture to become detached from the anchor prematurely.

Accordingly, a need exists for a threaded suture anchor to which suture is secured effectively so as to prevent detachment of the suture and eliminate anchor "pull back." In addition, a need exists for suture anchors having eyelets that will not abrade tissue and do not require countersinking. Suture anchors having a small core diameter providing maximum pullout strength even in soft bone and maximum suture fixation strength are also needed.

SUMMARY

In an embodiment, a suture anchor includes an anchor body having a longitudinal axis, a proximal end, and a distal end. The anchor body includes a central bore located at the proximal end and a passage extending between the central bore and the distal end. The central bore has a first dimension substantially perpendicular to the longitudinal axis, and the passage has a second dimension substantially perpendicular to the longitudinal axis less than the first dimension. The suture anchor includes a flexible strand extending through the passage, and a first knot formed in the flexible strand at the distal end has a third dimension greater than the second dimension to prevent the first knot from passing through the passage. A closed loop positionable at least partially within the central bore of the anchor body is configured to be formed entirely by the flexible strand without forming any additional knots on portions of the flexible strand extending proximally from the first knot.

In another embodiment according to any of the previous embodiments, the closed loop is positionable completely within the anchor body.

In another embodiment according to any of the previous embodiments, the closed loop is located within the central bore of the anchor body.

In another embodiment according to any of the previous embodiments, the central bore has an opening configured to receive a driver head for driving the suture anchor.

In another embodiment according to any of the previous embodiments, at least one suture strand is configured to pass slidingly through the flexible strand.

In another embodiment according to any of the previous embodiments, the anchor body is threaded from the proximal end to the distal end.

In another embodiment according to any of the previous embodiments, the anchor body comprises a bioabsorbable material.

In another embodiment according to any of the previous embodiments, the flexible strand includes a suture formed of ultrahigh molecular weight polyethylene.

In another embodiment according to any of the previous embodiments, the first knot is coated with a glue material.

In another embodiment according to any of the previous embodiments, a distal surface of the central bore is substantially perpendicular to the longitudinal axis of the suture anchor.

In another embodiment according to any of the previous embodiments, the anchor body is a single, integral, monolithic component.

In another exemplary embodiment, a suture anchor assembly for attachment of tissue to bone includes a suture anchor including an anchor body having a distal end, a proximal end, a longitudinal axis, an outer surface, a central bore located at the proximal end, and a passage extending between the central bore and the distal end. The central bore has a first dimension substantially perpendicular to the longitudinal axis, and the passage has a second dimension substantially perpendicular to the longitudinal axis that is less than the first dimension. The suture anchor assembly also includes a first flexible strand that extends through the passage of the anchor body, and a first knot formed in the first flexible strand at the distal end of the anchor body has a third dimension greater than the second dimension to prevent the first knot from passing through the passage. A closed loop positionable at least partially within the central bore of the anchor body is configured to be formed entirely by the first flexible strand without forming any additional knots on portions of the first flexible strand extending proximally from the first knot. The suture anchor assembly also includes at least a second flexible strand attached to the suture anchor and configured to pass slidingly through the first flexible strand.

In another embodiment according to any of the previous embodiments, the closed loop is configured to be recessed from the proximal end of the anchor body by about one third the length of the anchor body.

In another embodiment according to any of the previous embodiments, the anchor body comprises a plurality of thread flights extending from the outer surface of the anchor body.

In another embodiment according to any of the previous embodiments, the anchor body has an outside diameter of about 5.5 mm.

In another exemplary embodiment, a method attaches a suture anchor assembly to a driver. The suture anchor assembly is configured to approximate tissue to bone and includes a suture anchor. The suture anchor includes an anchor body having a distal end, a proximal end, a longitudinal axis, a central bore located at the proximal end, and a passage extending between the central bore and the distal end. The central bore has a first dimension substantially perpendicular to the longitudinal axis, and the passage has a second dimension substantially perpendicular to the longitudinal axis that is less than the first dimension. The suture anchor assembly includes a first flexible strand that extends through the passage of the anchor body, and a first knot formed in the first flexible strand at the distal end of the anchor body has a third dimension greater than the second dimension to prevent the first knot from passing through the passage. A closed loop positionable at least partially within the central bore of the anchor body is configured to be formed entirely by the first flexible strand without forming any additional knots on portions of the first flexible strand extending proximally from the first knot. The suture anchor assembly includes at least a second flexible strand attached to the suture anchor and configured to pass slidingly through the first flexible strand. The method includes the steps of coupling the suture anchor assembly to the driver and threading ends of the second flexible strand through a cannula of the driver.

In another embodiment according to any of the previous embodiments, the second flexible strand further comprises a needle attached to one end.

In another embodiment according to any of the previous embodiments, comprising the step of securing the needle within a cavity of a handle of the driver.

Other features and advantages of the present invention will become apparent from the following description of the invention, which refers to the accompanying drawings.

BRIEF DESCRIPTION OF THE DRAWINGS

FIG. 7(*b*) is an enlarged view of the fully-threaded suture anchor of FIG. 7(*a*).

FIG. 8(*b*) is an enlarged view of the needles attached to the fully-threaded suture anchor of FIG. 8(*a*).

FIG. 9(*b*) is an enlarged view of the fully-threaded suture anchor of FIG. 9(*a*).

DETAILED DESCRIPTION

Figure 1:
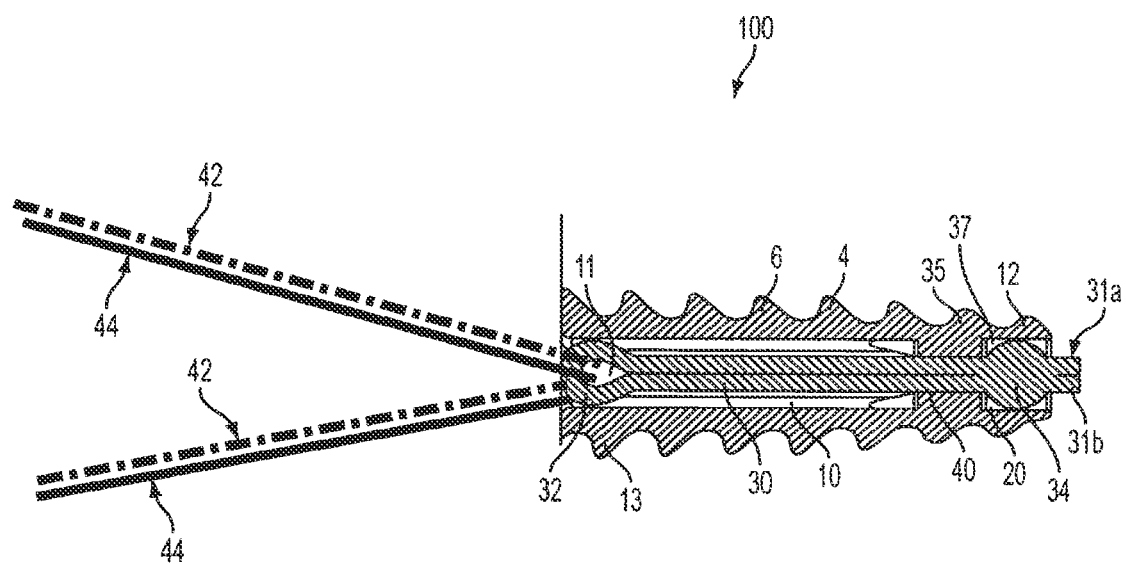
FIG. 1 is a cross-sectional view of a fully-threaded suture anchor according to the present invention, and with two suture strands looped through the internal loop of the fully-threaded suture anchor.
Figure 2:
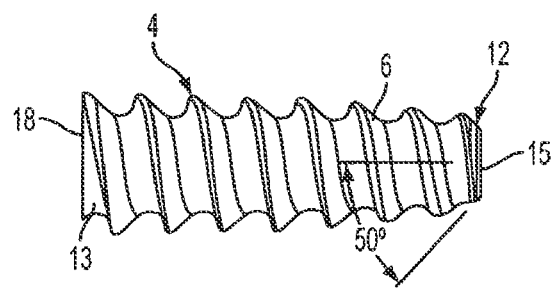
FIG. 2 is a perspective view of the fully-threaded suture anchor of FIG. 1, but without the two suture strands looped through the internal loop of the fully-threaded suture anchor shown in FIG. 1.
Figure 3:
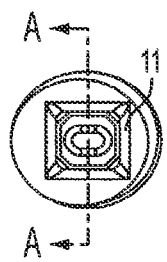
FIG. 3 is a proximal end view of the fully-threaded suture anchor of FIG. 2.

Referring now to the drawings, where like elements are designated by like reference numerals, FIGS. 1-6 illustrate a fully-threaded bioabsorbable suture anchor 100 of the present invention. The fully-threaded suture anchor 100 includes a body 4 provided in the shape of a tapered cylinder and having a distal end 12 and a proximal end 13.

As shown in FIG. 1, the fully-threaded suture anchor 100 is provided with a continuous thread 6 which wraps around the body 4 in a clockwise direction, the crest of the threads tapering from wide to narrow from the proximal to the distal end of the anchor. The proximal threads of anchor 100 with the widest crest surfaces are designed to engage the thin cortical shell in osteopenic bone to prevent anchor "pull back," which could cause the back of the anchor to be proud to the bone. In an exemplary embodiment, suture anchor 100 is provided with about eight thread flights wrapping around body 4, with the angle of the proximal surface of each thread being approximately between one-third and one-fourth the angle of the distal surface of each thread relative to the horizontal. For example, in the preferred embodiment, the proximal surface of each thread has an angle of 12° relative to a plane horizontal to the axis of the suture anchor, while the distal surface of each thread has an angle of 45° relative to the same horizontal plane.

By providing the suture anchor 100 with continuous threads running from the tip to the proximal end where the driver engages, the thread potential is maximized and the wasted space is minimized. The fully-threaded design of the anchor of the present invention substantially improves pull-out strength compared to suture anchors with protruding eyelets, and prevents anchor "pull-back" that can occur with countersunk anchors.

Figure 4:
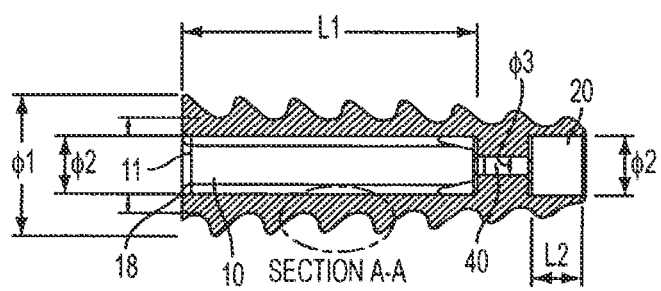
FIG. 4 is a cross-sectional view of the fully-threaded suture anchor of FIG. 2.
Figure 5:
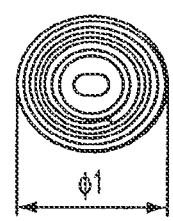
FIG. 5 is a distal end view of the fully-threaded suture anchor of FIG. 2.
Figure 6:
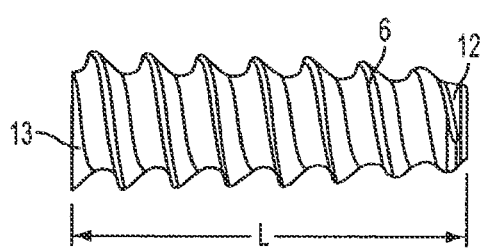
FIG. 6 is another perspective view of the fully-threaded suture anchor of FIG. 2.

As shown in FIGS. 1 and 4, the suture anchor 100 has a cylindrically shaped bore or socket 10 starting from a rectangularly shaped opening 11 at the proximal end and extending into the anchor body 4 approximately two-thirds of the length therethrough. Distally of the bore 10, anchor body is provided with a knot socket 20 which extends from the distal end 12 of the anchor. Knot socket 20 may have various shapes and configurations, for example, a cylindrical shape, as shown in FIG. 5. Bore 10 communicates with knot socket 20 through passage 40.

The proximal surface and associated edges of suture anchor 100 defining the rectangularly shaped opening 11 is rounded and smooth. Preferably, the proximal surface of the suture anchor 100 forming the periphery of the opening 11 forms a rounded lip 18 (FIG. 4) so that opening 11 has a slightly wider diameter than the main portion of the cylindrical bore 10. With the smooth and rounded proximal end provided in the anchor of the present invention, sutures threaded through the bore 10 and opening 11 will not be abraded by any sharp edges, and will not become frayed upon pressure or rubbing against the anchor at the proximal opening.

In a preferred embodiment, diameter $Ø_2$ (FIG. 4) of opening 11 is substantially equal to that of the knot socket 20, but larger than diameter $Ø_3$ of the passage 40 and smaller than outside diameter $Ø_1$ of the anchor body 4. Preferably, the outside diameter $Ø_1$ of the anchor body 4 is about 3 to about 8 mm, more preferably of about 5.5 mm, and the diameter $Ø_2$ of the opening 11 and socket 20 of about 1.5 to about 4.5 mm, more preferably of about 3 mm. In an exemplary embodiment, body 4 of suture anchor 100 has a length of about 0.6 in. and an exterior diameter of about 0.22 in. (5.5 mm) as measured across the outer diameter of the threading at the proximal end of the anchor.

Referring back to FIG. 1, a flexible strand 30, preferably suture, is threaded into the anchor body 4, with one end of the suture strand being threaded through the socket 20, passage 40 and bore 10 to form a loop or eyelet 32 located at least partially within bore 10 at the proximal end 13 of the anchor 100. Ends 31a, 31b extending through the anchor from the distal end 12 of the suture anchor are tied to form at least one knot 34.

In the preferred embodiment illustrated in FIG. 1, the loop 32 is completely recessed from the proximal end 13 of the anchor body 4. However, the invention also contemplates embodiments according to which the loop 32 extends out of the suture anchor 100 by a distance of about 0.5 to about 1.5 mm, more preferably of about 1 mm. In alternative configurations, the loop 32 may be also located completely outside of the bore 10 of the anchor 100. Thus, although the embodiment of FIG. 1 illustrates eyelet 32 disposed completely within the anchor body 4, this embodiment is only illustrative and the invention is not limited to it. The position and size of the eyelet of the present invention is determined according to the characteristics of the arthroscopic procedure, and the need to precisely orientate the eyelet during anchor insertion to optimize suture sliding characteristics.

The fully-recessed loop 32 of FIG. 1 has the ability to self-align, eliminating the need to determine eyelet alignment as it applies to the orientation of the tissue edge. The fully-recessed loop 32 also enhances suture slideability compared to conventional anchors with protruding eyelets, and allows the suture to slide against the smooth inner edge of the anchor reducing the potential for suture abrasion from the cortical bone edge.

At the distal end 12 of anchor 100, flexible strand of material 30 forms at least one knot 34, which is preferably an over-hand knot. Knot 34 is housed in the knot socket 20 and rests on most distal surfaces 37 of regions 35 of the anchor body 4 that define the passage 40 having a diameter narrower than that of the sockets 10 and 20. To increase the pull out strength of the strand 30 from the anchor, knot 34 may be optionally coated with a glue material to increase its strength and facilitate adherence to the walls of the socket 20. Knot 34 increases the pullout strength of the strand even in soft bone, provides increased fixation, and eliminates the anchor "pull back."

The strand 30 may be formed of any flexible material. In the preferred embodiment, strand 30 and loop 32 are formed of a high strength suture material such as the one described in U.S. Pat. No. 6,716,234 to Grafton et al., the disclosure of which is incorporated by reference in its entirety. In additional embodiments, the strand 30 may be insert-molded into the anchor in the manner described in U.S. Pat. No. 5,964,783 to Grafton et al., the disclosure of which is also incorporated by reference in its entirety.

The anchor body 4 is preferably formed of a translucent or transparent polymer material, and is preferably made of bioabsorbable materials such as polyglycolic or polylactic acid polymers. Accordingly, flexible strand 30 is visible through the body of the fully-threaded anchor 100 to provide visual confirmation of strand encapsulation within the anchor. Advantageously, the flexible strand of material 30 and the anchor body 4 are made of materials selected such that the loop 32 will not biodegrade before anchor body 4. As used in the present application, the term "bioabsorbable" is considered to be interchangeable with the term "biodegradable," "resorbable," and "absorbable" to mean that the device can be absorbed by the body over time. Also, the measurements, angles and ratios between the dimensions of the suture anchor may be varied from those described above so as to be suitable for the conditions and applications in which the suture anchor is to be used.

Optionally, the suture anchor can be distributed with at least one strand of suture already threaded through the loop 32. For example, FIG. 1 illustrates suture strands 42, 44 attached to the loop allowing the sutures to slide smoothly with minimal friction. In an exemplary embodiment, the suture strands 42, 44 may be FiberWire composite sutures of alternating colors to maximize repair strength, aid in suture management and provide superior tying characteristics.

Figure 7A:
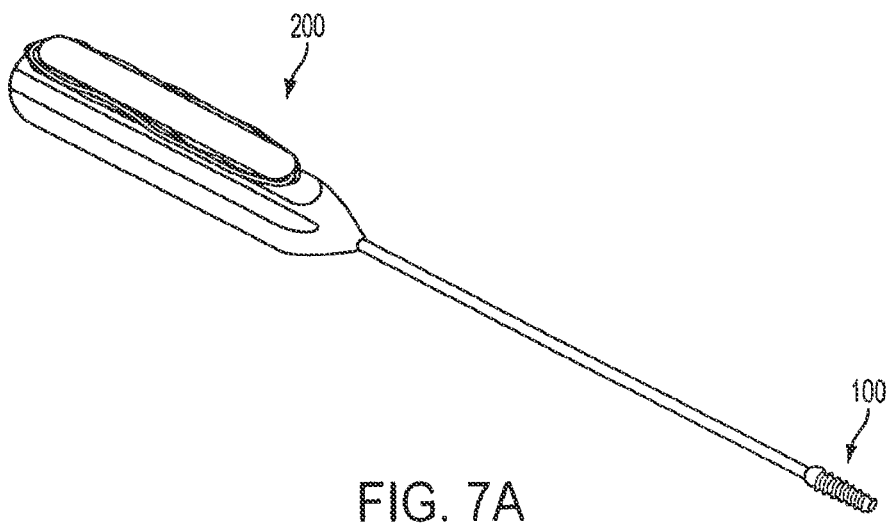
FIG. 7(*a*) is a perspective view of a first exemplary embodiment of a cannulated driver preloaded with the fully-threaded suture anchor of FIGS. 1-6.
Figure 7B:
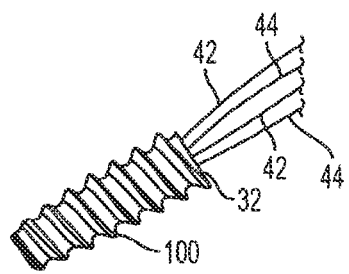
Figure 8A:
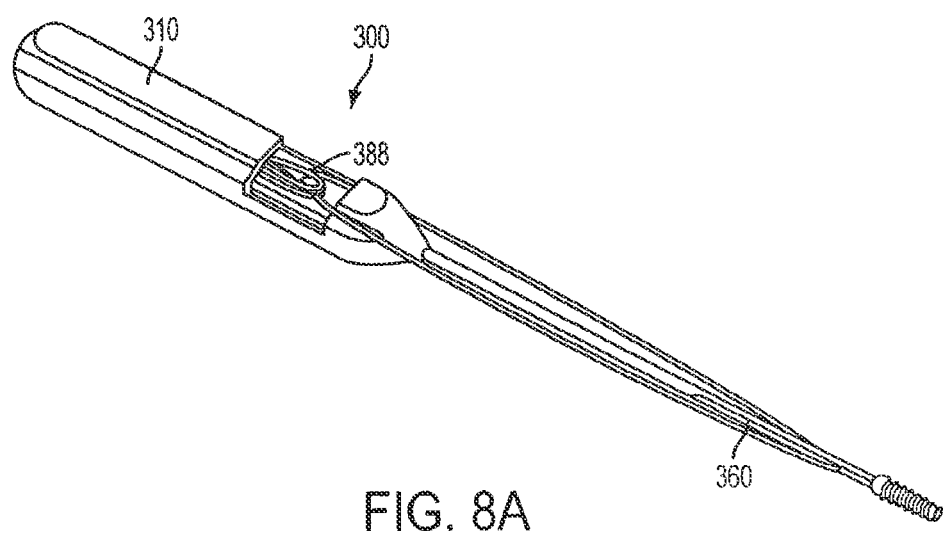
FIG. 8(*a*) is a perspective view of a second exemplary embodiment of a driver preloaded with the fully-threaded suture anchor of the present invention, and with needles attached to the two suture strands looped through the internal loop of the fully-threaded suture anchor.
Figure 9A:
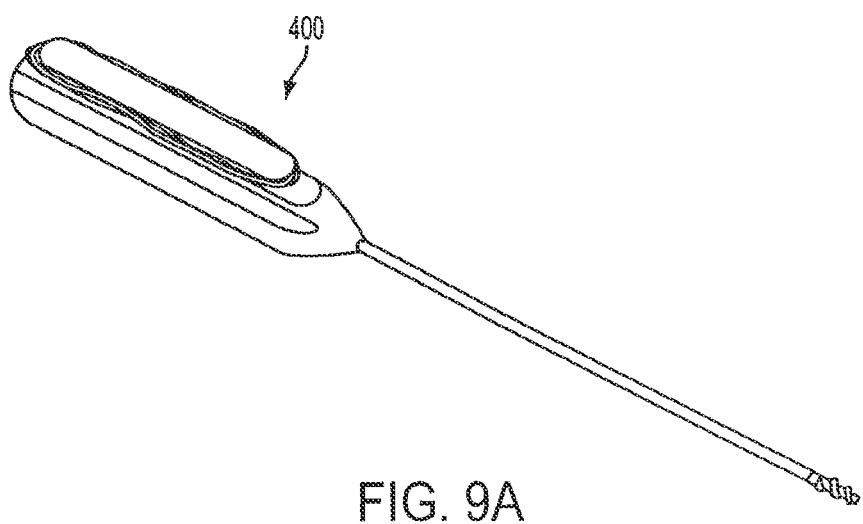
FIG. 9(*a*) is a perspective view of a third exemplary embodiment of a driver preloaded with the fully-threaded suture anchor of the present invention, and with punch needles attached to the two suture strands looped through the internal loop of the fully-threaded suture anchor.

FIGS. 7(a), 8(a) and 9(a) illustrate various embodiments of drivers 200, 300, 400 used to install the fully-threaded suture anchor 100 of the present invention. FIG. 7(a) illustrates cannulated driver 200 preloaded with the fully-threaded suture anchor of FIGS. 1-6 and with suture strands 42, 44 attached to the loop 32. As explained in more detail below with reference to FIGS. 10-15 and 23-26, suture strands 42, 44 are threaded through the cannula of the driver 200 and secured on a hook on the handle of the driver, to allow the distal end of the head of the driver to be inserted into the opening 11 and bore 10 of the anchor 100 so that the suture anchor is driven into a pilot hole.

FIG. 8(a) illustrates a second embodiment of a driver of the present invention. Driver 300 (which will be described in more detail in FIGS. 16-22) is not cannulated, but rather presented with a slot or side cannulation 360 in the shaft 330. The slot allows suture strands that are provided with needles 380 (FIG. 8(b)) and that are attached to the loop 32 of the anchor 100 to pass through the slot and around the sides of handle 310, to be further secured in needle slot 388 of the handle.

Figure 9B:
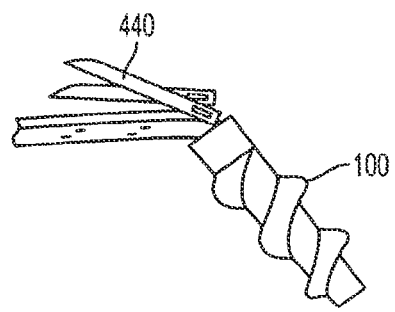
Figure 10:
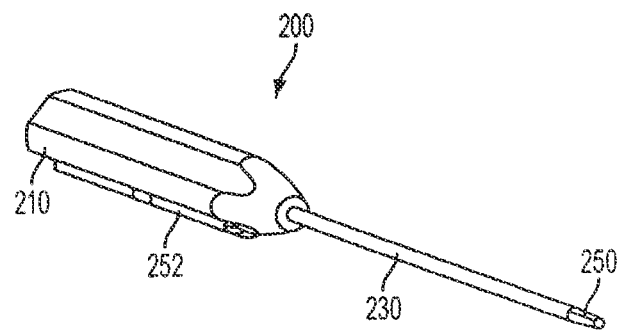
FIG. 10 is a perspective view of the cannulated driver shown in FIG. 7(*a*).
Figure 11:
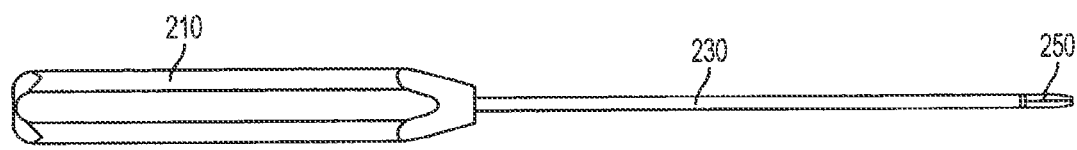
FIG. 11 is another perspective view of the cannulated driver of FIG. 10.
Figure 12:
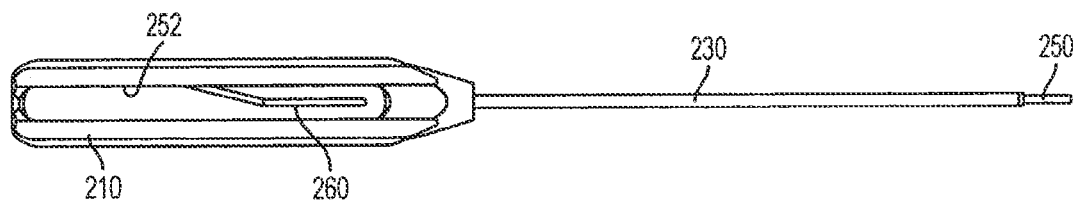
FIG. 12 is a side view of the cannulated driver of FIG. 11.
Figure 13:
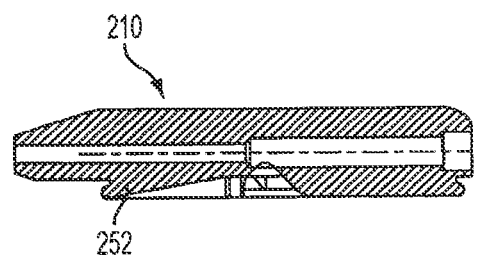
FIG. 13 is a cross-sectional view of the handle of the cannulated driver of FIG. 10.
Figure 14:
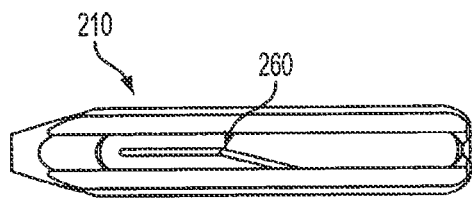
FIG. 14 is a side view of the handle of the cannulated driver of FIG. 10.
Figure 15:
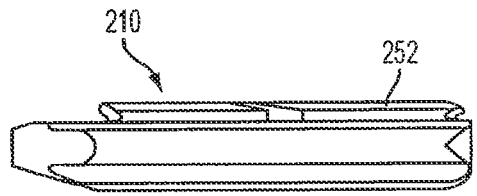
FIG. 15 is a top view of the handle of the cannulated driver of FIG. 10.
Figure 16:
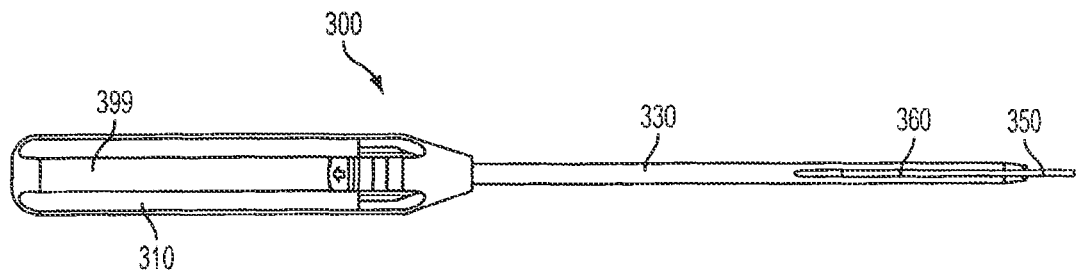
FIG. 16 is a top view of the driver shown in FIG. 8(*a*).
Figure 17:
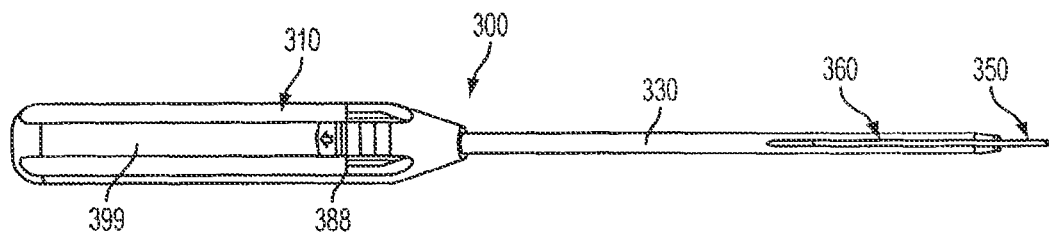
FIG. 17 is a perspective view of the driver shown in FIG. 16.
Figure 18:
FIG. 18 is a side view of the shaft and head of the driver shown in FIG. 16.
Figure 19:
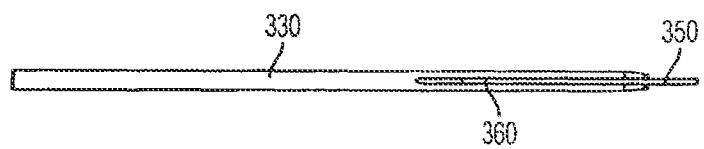
FIG. 19 is a top view of the shaft and head shown in FIG. 18.

FIG. 9(a) illustrates yet another embodiment of a driver of the present invention, according to which driver 400 is employed in connection with suture strands with punch needles 440 (FIG. 9(b)) that are attached to the loop 32 of the anchor 100 of the present invention.

FIGS. 10-15 illustrate details of the first exemplary embodiment of driver 200 used to install the fully-threaded suture anchor 100 of the present invention during an arthroscopic procedure. The driver 200 is provided with a head 250, a shaft 230 and a handle assembly 210. The head 250 of the driver is configured to be received within anchor socket 10 of the fully-threaded suture anchor 100 of FIGS. 1-6. In an exemplary embodiment, the drive head is rectangularly shaped and has a width and a length which substantially corresponds to the width and length of opening 11 in suture anchor 100. Preferably, the drive head is slightly shorter and has a slightly smaller width than opening 11, so that the fit is not too tight, yet ensures secure engagement for driving the suture anchor into bone.

The shaft 230 preferably comprises an elongate, narrow diameter body suitable for use in remote procedures performed through percutaneous tissue punctures, such as arthroscopic, laparoscopic and other invasive procedures and the like. The shaft typically has a length of about 5 cm to about 20 cm, preferably about 15 cm. The diameter of the shaft assembly is sufficiently small to facilitate introduction through access sheaths, cannulas, trocars, and the like, typically being less than about 10 mm, preferably about 5 mm.

The handle assembly 210 preferably includes an elongated double hook 252 extending substantially along the length thereof and having a hook at the proximal end and at the distal end thereof, and a clip 260 formed at one end region of the double hook 252. As explained in more detail below with reference to FIGS. 23-26, when driver 200 is engaged with suture anchor 100, excess lengths of suture 42, 44 passed through the proximal end of driver 200 can be wrapped around the double hook 252, and the ends of the sutures can be secured in the clip 260. In this manner, the suture strands 42, 44 can be prevented from becoming tangled or otherwise interfering with the surgeon's work.

Driver 200 is preferably constructed to withstand an application of about 20 in/lb of torque. Preferably, although not necessarily, at least the shaft and drive head are made of stainless steel. However, other materials may be used which provide the necessary strength and rigidity for installing the suture anchor of the present invention into cortical bone.

The anchor 100 and driver 200 may be provided to the surgeon as a preformed assembly with the sutures 32, 34 pre-threaded through loop 32 and through the cannula of the driver and secured on the handle.

FIGS. 16-22 illustrate details of the second exemplary embodiment of driver 300 used to install the fully-threaded suture anchor 100 of the present invention during an arthroscopic procedure, preferably during an open procedure such as mini-open rotator cuff repairs. The driver 300 is different from the driver 200 described above in that driver 300 allows installation of a fully-threaded suture anchor that has attached at least one strand of suture with a surgical needle. Thus, driver 300 is not cannulated but rather comprises a slot or side cannulation 360 provided for about half the length of the shaft 330 and defined by break edges 350. The side cannulation allows suture strands 342, 344 (FIG. 8(b)), which are received in the cannulation, to be provided with surgical needles 380 (FIG. 8(b)) at one end, which would not be possible if the driver had a central (fully closed) cannulation.

Figure 8B:
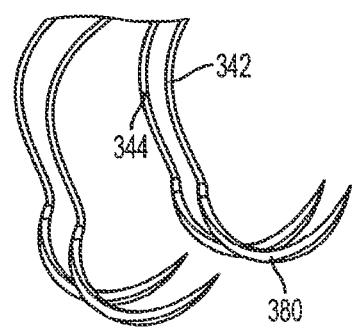

When driver 300 is engaged with suture anchor 100, excess lengths of suture 342, 344 with attached needles 380 can be secured in recess region or cavity 388 (FIG. 8(b)) of the handle 310. The cavity 388 is accessed by opening a pivotable hatch 399. In this manner, the needles 380 and suture strands 342, 344 are wrapped around tie-down bars disposed in the inside of the housing cavity when the hath is closed. Thus, surgical needles 380 may be safely stored within the handle 310, preventing therefore any piercing of surgical gloves and any problems in maintaining the needles sterile.

Figure 20:
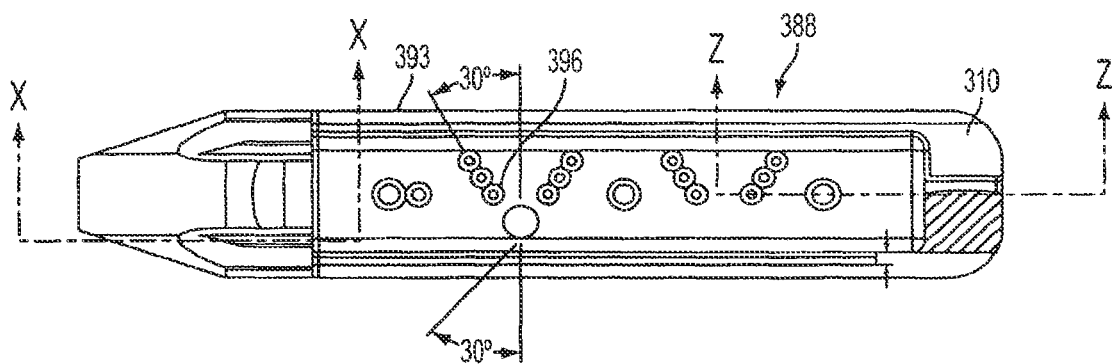
FIG. 20 is a top view of the handle of the driver of FIG. 16, with the cover removed.
Figure 21:
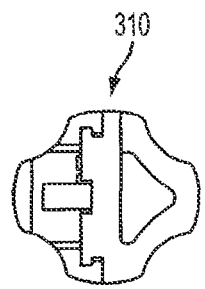
FIG. 21 is a proximal end view of the handle shown in FIG. 20.
Figure 22:
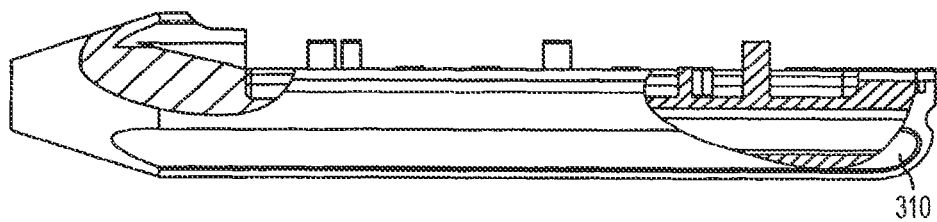
FIG. 22 is a partial cross-sectional side view of the driver of FIG. 20.

FIGS. 20-23 illustrate details of the housing cavity 388 provided in the handle 310 of the driver 300. As shown in FIG. 20, cavity 388 is provided with a plurality of slots 396 and tie-down bars 393, that allow the surgical needles 380 to be "parked" or secured within the slots and the bars. If desired, a plurality of sutures with or without needles may be housed within the housing cavity 388. The cavity 388 is accessed by opening the pivotable hatch 399. Driver 300 is also configured to be received within anchor opening 11 of the fully-threaded suture anchor 100 of FIGS. 1-6.

Figure 23:
FIG. 23 illustrates a schematic view of the fully-threaded suture anchor of FIG. 1, having a recessed loop, and with two suture strands looped through the internal loop of the fully-threaded suture anchor.
Figure 24:
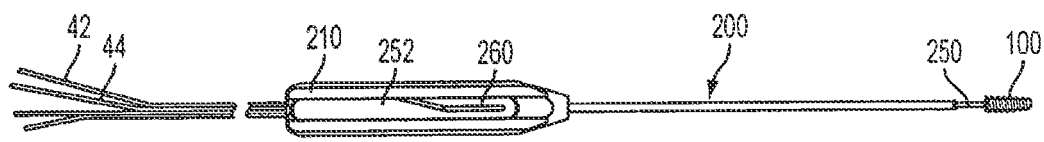
FIG. 24 illustrates a top view of the cannulated driver of FIGS. 10-15 loaded with the fully-threaded suture anchor of FIG. 23, and with the two suture strands threaded through the cannula of the driver.
Figure 25:
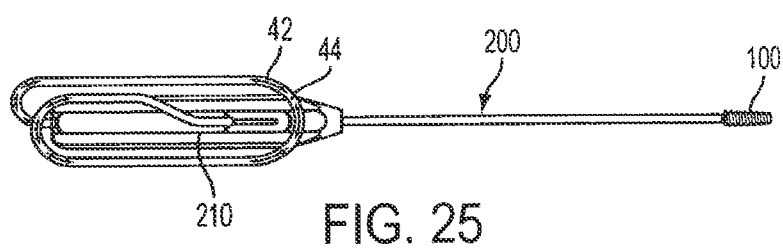
FIG. 25 illustrates a top view of the cannulated driver of FIGS. 10-15 loaded with the fully-threaded suture anchor of FIG. 23, and showing the loading path of the two suture strands threaded through the cannula of the driver.
Figure 26:
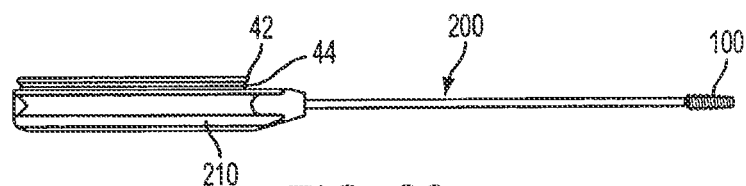
FIG. 26 illustrates a side view of the cannulated driver of FIGS. 10-15 loaded with the fully-threaded suture anchor of FIG. 23, and showing the two suture strands threaded through the cannula of the driver and secured to the driver.
Figure 27:
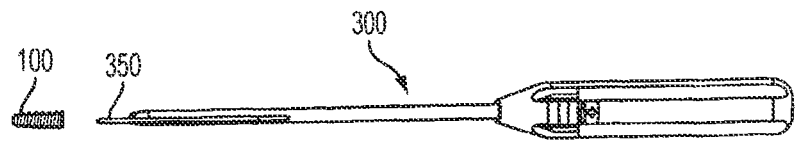
FIG. 27 illustrates a side view of the driver shown in FIGS. 16-22 before being loaded with the fully-threaded suture anchor having two suture strands with attached needles.
Figure 28:
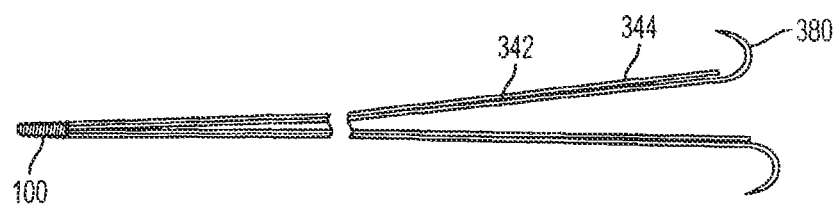
FIG. 28 illustrates a schematic view of the fully-threaded suture anchor of FIG. 1, having a recessed suture loop and two suture strands looped through the loop of the fully-threaded suture anchor, the two suture strands having attached needles.

FIGS. 23-26 illustrate the cannulated driver of FIGS. 10-15 loaded with the fully-threaded suture anchor of FIG. 23. As shown in FIG. 24, the two suture strands 42, 44 are first threaded through the cannula of the driver 200, and the distal end of the drive head 250 (FIG. 24) of the driver is then inserted into the opening 11 of the anchor 100. The sutures exiting the proximal end of driver 200 are wrapped around the double hook 252 and/or clipped in clip 260.

Figure 29:
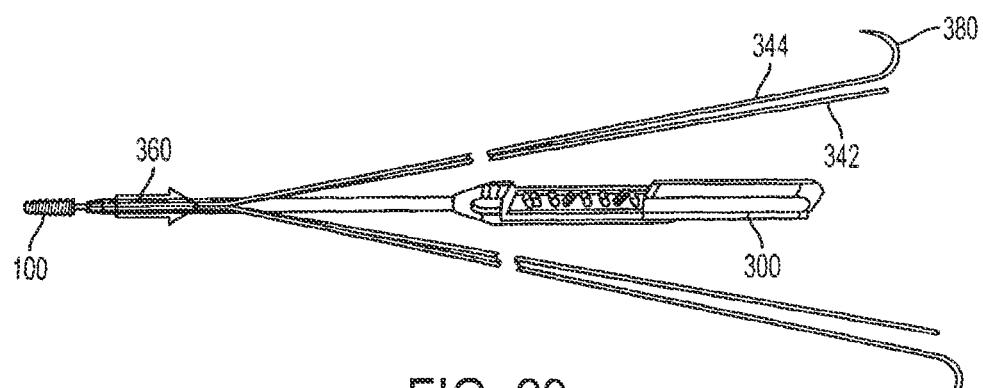
FIG. 29 illustrates a perspective view of the driver of FIG. 27 loaded with the fully-threaded suture anchor of FIG. 28, and with the two suture strands with attached needles partially threaded through a side cannulation of the driver.
Figure 30:
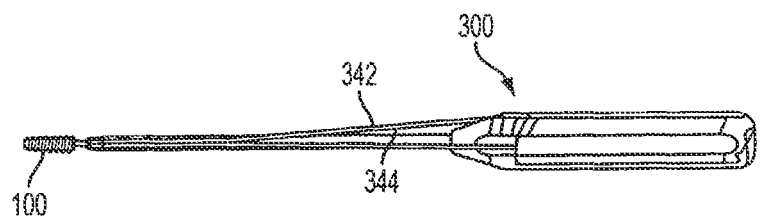
FIG. 30 illustrates another perspective view of the driver of FIG. 27 loaded with the fully-threaded suture anchor of FIG. 28 and with the two suture strands and attached needles secured to the driver.

FIGS. 27-30 illustrate the driver 300 of FIGS. 16-22 loaded with the fully-threaded suture anchor 100 and provided with two suture strands 342, 344 having attached surgical needles 380. As shown in FIG. 29, the two suture strands 342, 344 are first passed through side cannulation 360 of the shaft of the driver 300, so that the distal end of the drive head 350 of the driver is then inserted into the opening 11 of the anchor 100. The sutures passed through the side cannulation are pulled toward the proximal end of the driver 300 and the suture strands 342, 344 are wrapped around the tie-down bars 393 in the housing cavity 388, while the needles 380 are stored within slots 396.

Sutures anchors according to the present invention can be used for arthroscopic procedures. The anchors are also advantageous for open and mini-open surgical procedures. Specific examples of applicable procedures include cortical bone-soft tissue fixation, Bankart and SLAP shoulder repairs.

Figure 33:
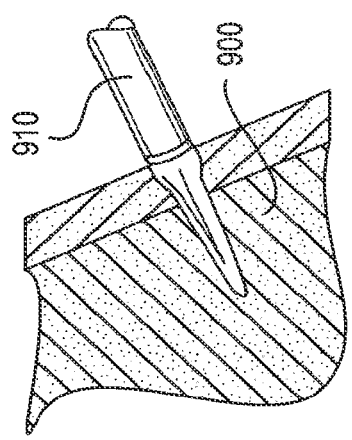
FIG. 33 is a schematic cross-sectional view of a bone fragment undergoing a suture anchor installation in accordance with a method of the present invention and at an initial stage.
Figure 34:
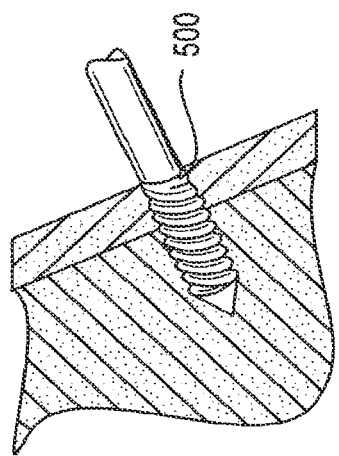
FIG. 34 illustrates the bone fragment of FIG. 33 at a stage of suture anchor installation subsequent to that shown in FIG. 33.

An exemplary method of employing the suture anchors of the present invention is described below with reference to FIGS. 33-36. FIG. 33 illustrates a schematic cross-sectional view of bone segment 900 which undergoes suture anchor installation according to the present invention. A punch 910 (FIG. 33) either alone or in combination with tap 500 (FIG. 34) may be employed for forming a hole in bone 900 into which suture anchor 100 is to be inserted. If bone 900 is soft bone, punch 910 may be sufficient for drilling the hole. If, however, the bone is hard cortical bone, the punch/tap combination may be desirable. Preferably, the diameter of the hole formed is slightly (e.g. 1 mm) smaller than the diameter of the suture anchor to be installed, to ensure good purchase of the suture anchor threads in the bone. Alternatively, a self-drilling/self-tapping suture anchor can be formed and inserted directly into bone by engaging the anchor with a driver and turning the anchor to advance the anchor directly into bone without previous formation of a hole.

Figure 31:
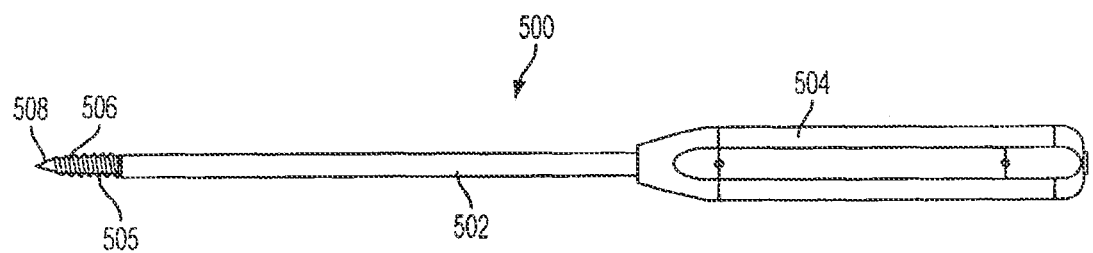
FIG. 31 is a perspective view of a punch employed to create a pilot hole for the fully-threaded suture anchor of the present invention.
Figure 32:
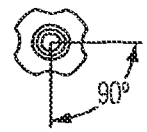
FIG. 32 is a distal end view of the punch of FIG. 31.

FIGS. 31 and 32 illustrate an embodiment of tap 500 employed to prepare a bone socket or pilot hole prior to insertion of the anchor. As shown in FIGS. 31 and 32, tap 500 includes a shaft 502 having a handle 504 on a proximal end and a tapping head 506 on a distal end. Tapping head 506 includes a trocar tip 508 followed by a tapered, spiral cutting section 505. Using tap 500, a hole for the suture anchor is formed to accommodate a head of a cannulated driver used to install the suture anchor.

Figure 36:
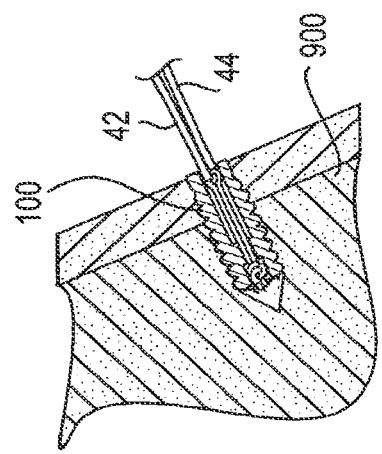
FIG. 36 illustrates the bone fragment of FIG. 33 at a stage of suture anchor installation subsequent to that shown in FIG. 35.
Figure 35:
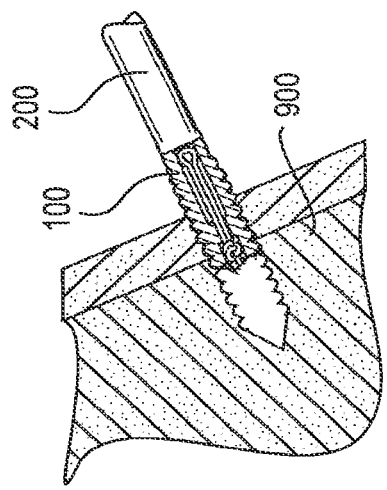
FIG. 35 illustrates the bone fragment of FIG. 33 at a stage of suture anchor installation subsequent to that shown in FIG. 34.

Reference is now made to FIGS. 35 and 36. Driver 200 loaded with the fully-threaded suture anchor of the present invention (shown in FIG. 26, for example) is then placed at the opening of the prepared hole in bone 900, and the driver 200 is rotated until the proximal surface of the anchor 100 is flush with the surface of the bone. The driver tip is then pulled back, to reveal the suture strands 42, 44 (FIG. 36). Since it is not necessary for the proximal end of the anchor to be countersunk below the bone surface to prevent tissue abrasion, the inventive anchor does not need to be inserted as far as prior art devices, and avoids abrasion of the sutures by the rim of the bone around the installed suture anchor.

The suture anchor of the present invention provides advantages in addition to those already discussed above. For example, with the threads provided along the entire length of the suture anchor body, the anchor is afforded maximum securement by the threads in the cortical bone, unlike some prior art anchors in which the threads only contact the cancellous bone. Also, by providing a knot which is optionally coated with a glue material, the suture anchor is installed with a higher torque than many prior art anchors, and thus has improved fixation strength.

Although the present invention has been described in relation to particular embodiments thereof, many other variations and modifications and other uses will become apparent to those skilled in the art.

What is claimed is:

1. A suture anchor comprising:
an anchor body having a longitudinal axis, a proximal end, and a distal end, wherein the anchor body defines a first central bore located at the proximal end and having a first dimension measured substantially perpendicular to the longitudinal axis, a second central bore located at the distal end and having a second dimension measured substantially perpendicular to the longitudinal axis, and a passage extending between the first and second central bores and having a third dimension measured substantially perpendicular to the longitudinal axis that is less than both the first and second dimensions; and
a flexible strand forming a knot positionable in the second central bore with a fourth dimension greater than the third dimension to prevent the knot from passing through the passage;
wherein the flexible strand extends from the knot through the passage to the first central bore and is configured to form a closed loop positionable at least partially within the first central bore, and wherein the passage extends radially away from the longitudinal axis by a distance that is greater than a thickness of a first segment of the flexible strand that extends through the passage such that the entire first segment of the flexible strand that extends through the passage is configured to be spaced apart from the longitudinal axis.

2. The suture anchor of claim 1, wherein the closed loop is positionable completely within the anchor body.

3. The suture anchor of claim 1, wherein the closed loop extends from the knot through the passage into the first central bore and back through the passage to the knot.

4. The suture anchor of claim 1, wherein the knot forms part of the closed loop.

5. The suture anchor of claim 1, wherein the closed loop is configured to be formed entirely by the flexible strand without forming any additional knots on portions of the flexible strand extending proximally from the first knot.

6. The suture anchor of claim 1, wherein a second segment of the flexible strand is configured to extend through the passage adjacent to the first segment of the flexible strand.

7. The suture anchor of claim 1, wherein the passage has an elongate cross-sectional shape in a plane perpendicular to the longitudinal axis to facilitate the spacing apart of the first segment of the flexible strand from the longitudinal axis.

8. The suture anchor of claim 1, further comprising at least one suture strand configured to pass slidingly through the flexible strand.

9. The suture anchor of claim 1, wherein the anchor body further comprises an outer surface and a thread formed on at least part of the outer surface.

10. The suture anchor of claim 1, wherein the longitudinal axis is configured to extend through a center of the knot.

11. A suture anchor comprising:
an anchor body having a longitudinal axis, a proximal end, and a distal end, wherein the anchor body defines a first central bore located at the proximal end and having a first dimension measured substantially perpendicular to the longitudinal axis, a second central bore located at the distal end and having a second dimension measured substantially perpendicular to the longitudinal axis, and a passage extending between the first and second central bores and having a third dimension measured substantially perpendicular to the longitudinal axis that is less than both the first and second dimensions; and
a flexible strand forming a knot positionable in the second central bore with a fourth dimension greater than the third dimension to prevent the knot from passing through the passage;
wherein the flexible strand extends from the knot through the passage to the first central bore and is configured to form a closed loop positionable at least partially within the first central bore, and wherein the passage has an elongate cross-sectional shape in a plane perpendicular to the longitudinal axis, such that a first segment of the flexible strand that extends through the passage is movable away from the longitudinal axis by a first distance in a first radial direction while the first segment of the flexible strand is prevented by the passage from moving away from the longitudinal axis to the first distance in a different second radial direction.

12. The suture anchor of claim 11, wherein the closed loop is positionable completely within the anchor body.

13. The suture anchor of claim 11, wherein the knot forms part of the closed loop.

14. The suture anchor of claim 11, wherein a second segment of the flexible strand is configured to extend through the passage adjacent to the first segment of the flexible strand.

15. The suture anchor of claim 11, further comprising at least one suture strand configured to pass slidingly through the flexible strand.

16. The suture anchor of claim 11, wherein the longitudinal axis is configured to extend through a center of the knot.

17. The suture anchor of claim 11, wherein the longitudinal axis extends through the passage.

18. The suture anchor of claim 11, wherein the passage has a closed end in the first radial direction and a closed end in a direction opposite the first radial direction.

19. The suture anchor of claim 18, wherein the passage extends a same radial distance from the longitudinal axis in the first radial direction and in a direction opposite the first radial direction.

20. The suture anchor of claim 11, wherein the anchor body further comprises an outer surface and a thread formed on at least part of the outer surface.

* * * * *